(12) United States Patent
Speetjens et al.

(10) Patent No.: US 10,392,639 B2
(45) Date of Patent: Aug. 27, 2019

(54) PROCESS FOR THE TREATMENT OF YEAST CELL WALLS WITH A LAMINARIPENTAOSE PRODUCING BETA-1,3-GLUCANASE

(71) Applicant: DSM IP Assets B.V., Heerlen (NL)

(72) Inventors: Ellen Speetjens, Echt (NL); Peter Philip Lankhorst, Echt (NL)

(73) Assignee: DSM IP Assets B.V., Heerlen (NL)

( * ) Notice: Subject to any disclaimer, the term of this patent is extended or adjusted under 35 U.S.C. 154(b) by 189 days.

(21) Appl. No.: 15/127,133

(22) PCT Filed: Mar. 20, 2015

(86) PCT No.: PCT/EP2015/055986
§ 371 (c)(1),
(2) Date: Sep. 19, 2016

(87) PCT Pub. No.: WO2015/140318
PCT Pub. Date: Sep. 24, 2015

(65) Prior Publication Data
US 2017/0107547 A1    Apr. 20, 2017

(30) Foreign Application Priority Data

Mar. 21, 2014   (EP) ..................................... 14161040

(51) Int. Cl.
| | | |
|---|---|---|
| *C12P 7/02* | (2006.01) | |
| *C12P 19/04* | (2006.01) | |
| *A61K 31/716* | (2006.01) | |
| *C08B 37/00* | (2006.01) | |
| *C12P 19/14* | (2006.01) | |
| *A23K 20/163* | (2016.01) | |
| *A23K 50/75* | (2016.01) | |
| *A23K 50/30* | (2016.01) | |
| *A61K 36/064* | (2006.01) | |

(52) U.S. Cl.
CPC ............ *C12P 19/04* (2013.01); *A23K 20/163* (2016.05); *A23K 50/30* (2016.05); *A23K 50/75* (2016.05); *A61K 31/716* (2013.01); *A61K 36/064* (2013.01); *C08B 37/0024* (2013.01); *C12P 19/14* (2013.01)

(58) Field of Classification Search
CPC .................................................... A61K 31/716
USPC ......................................................... 435/183
See application file for complete search history.

(56) References Cited

FOREIGN PATENT DOCUMENTS

| | | |
|---|---|---|
| CN | 101020915 A | 8/2007 |
| JP | 09262090 | 10/1997 |
| WO | 2011143613 A1 | 11/2011 |

OTHER PUBLICATIONS

Kenji Doi; "Purification and Properties of Lytic β-Glucanase from an Arthrobacter Bacterium"; The Institute of Scientific and Industrial Research, Osaka University, Suita, Osaka, Agr. Biol. Chem. 37(7), Dec. 11, 1972; pp. 1619-1627.
Ken-Ichi Ishibashi; "DNA array analysis of altered gene expression in human leukocytes stimulated with soluble and particulate forms of Candida cell wall β-glucan"; International Immunopharmacology 4; 2004; pp. 387-401.
Naohito Ohno; "Solubilization of yeast cell-wall β-(1-3)-D-glucan by sodium hypochlorite oxidation and dimethyl sulfoxide extraction"; Carbohydrate Research 316; 1999; pp. 161-172.
Kenji Doi; "Cloning and Expression in *Escherichia coli* of the Gene for an Arthrobacter β-(1-3)-Glucanase"; Journal of Bacteriology, Dec. 1986; vol. 168; No. 3; pp. 1272-1276 (XP-002729892).
S.D. Bentley; AL939132; SV 1; linear; genomic DNA; STD; PRO; 302007 BP; XP-002729895.
ENA Sequence: D23668 | dbfetch | EBI; XP-002729896.
International Search Report dated Aug. 25, 2015 as cited in the related International Patent Application No. PCT/EP2015/055986.
M. Vrsanska; "Enzymes of the yeast lytic system produced by Arthrobacter GJM-1 bacterium and their role in the lysis of yeast cell walls"; Zeitschrift für Allgemeine Mikrobiologie, Institute of Chemistry, Slovak Academy of Sciences, Bratislava, Czechoslovakia; 1977; vol. 17, No. 6; pp. 465-480 (XP-002729893).
M. Vrsanska; "Lysis of intact yeast cells and isolated cell walls by an inducible enzyme system of Arthrobacter GJM-1", Zeitschrift für Allgemeine Mikrobiologie, Institute of Chemistry, Slovak Academy of Sciences, Bratislava, Czechoslovakia; 1997, vol. 17; No. 5; pp. 391-402 (XP-002729894).

*Primary Examiner* — Tekchand Saidha
(74) *Attorney, Agent, or Firm* — McBee Moore Woodward & Vanik IP, LLC

(57) ABSTRACT

The present invention provides a process for the treatment of a composition comprising yeast cell walls comprising β-1, 3-glucans which are insoluble when extracted with water and partially soluble when extracted with DMSO, the process comprising contacting said composition with laminaripentaose-producing-β-1,3-glucanase and inactivating the laminaripentaose-producing-β-1,3-glucanase to result in a composition comprising yeast cell walls wherein the β-1,3-glucans have an improved solubility in DMSO and the ratio of β-glucans soluble in DMSO compared to water is greater than or equal to 2.

12 Claims, 5 Drawing Sheets
Specification includes a Sequence Listing.

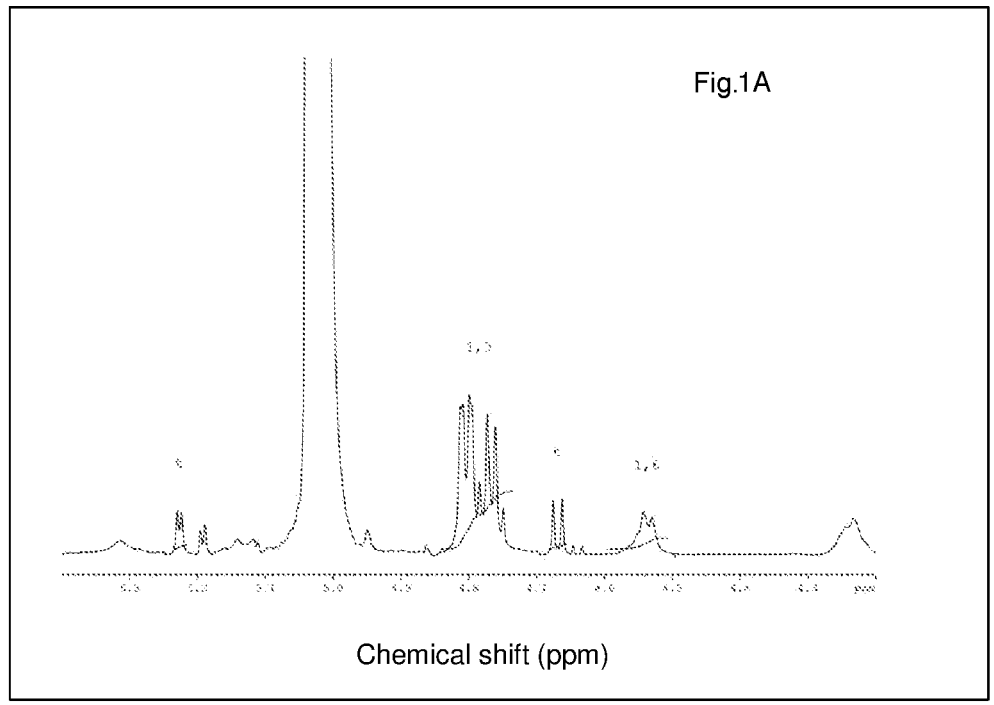
Chemical shift (ppm)
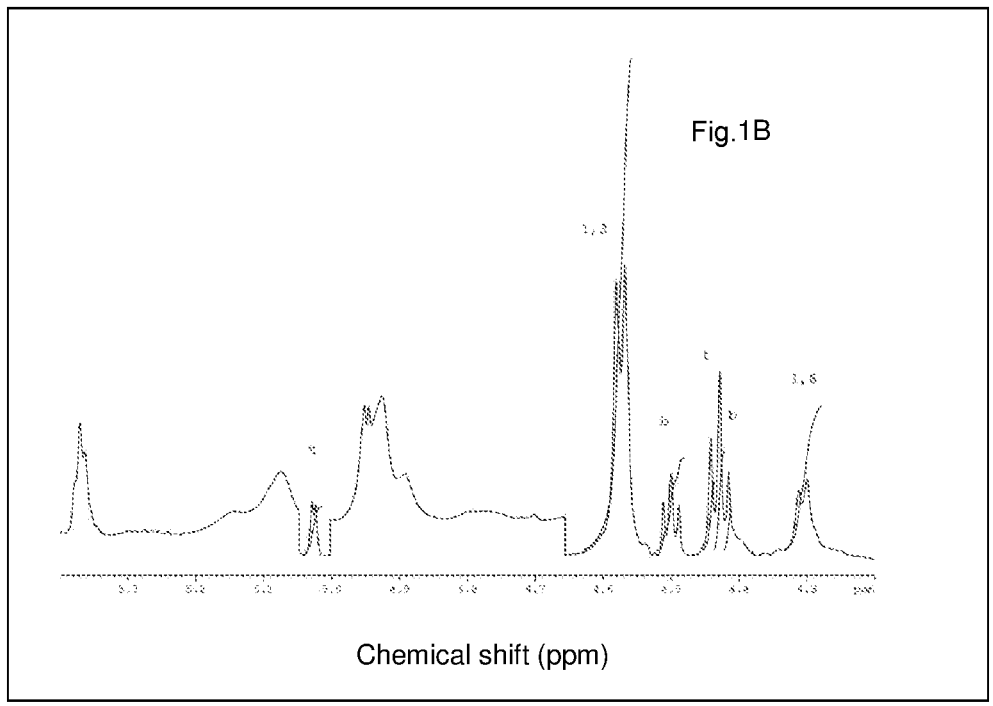
Chemical shift (ppm)

MLSRLRHRLLAVAAAAGLTGALLSFGAAPPADAAVPATIPLKITNNSARGDAVHIYNLGT
SLTTGQQGWADENGTFHAWPAGGNPPTPAPDASIPGPAAGQTKTIRIPKLSGRIYFSY
GQKLDFRLTTGGLVQPAVQNPSDPNRNILFNWSEYTLNDGGLWLNSTQVDMFSAPYT
VGVQRADGGVTSAGQLKAGGYRGVFDALRAQPGWGGLIQTRPDGTVLRALAPLYGVE
TGALPASVMDDYINRVWQKYTTTTLTVTPFGDRPDTKYFGRVSGNVMNFTNTSGAVVT
SFQKPDASSVFGCHRLLDAPNDQVRGPISRTLCAGFNRSTLLSNPNQPDPSAANFYRD
PVTNHYARIIHERMADGKAYAFAFDDVGNHESLVHDGNPAEARLTLAPLD

Fig. 2

MLRTLRRRVTAVALGLATALGGGWLAAGVPSPAHAAVPATIPLTITNNSGRAEQIHIYNL
GTELSSGRQGWADASGAFHPWPAGGNPPTPAPDASIPGPAPGRSTTIQIPKFSGRIYF
SYGRKMEFRLTTGGLVQPAVQNPTDPNRDILFNWSEYTLNDSGLWINSTQVDMFSAPY
TVGVRRGDGTTLSTGKLRPGGYNGVFNALRGQSGGWANLIQTRSDGTVLRALSPLYG
VETGALPASVMDDYINRVWNKYTGTDLIVTPFADRPDVRYTGRVSGGVLRFTDGSGAV
VTTFQKPDASSVFGCHRLLDAPNDQVRGPISRTLCAGFNRTTLLANPHQPDRSAAGFY
QEPVTNHYARIIHAHMADGKAYGFAFDDVGHHESLVHDGDPRGASLTLDPFD

Fig. 3

SEQUENCE LISTING

<160> NUMBER OF SEQ ID NOS: 7

<210> SEQ ID NO 1
<211> LENGTH: 8
<212> TYPE: PRT
<213> ORGANISM: Streptomyces coelicolor A3

<400> SEQUENCE: 1

```
Ile Tyr Phe Ser Tyr Gly Gln Lys
1               5
```

<210> SEQ ID NO 2
<211> LENGTH: 67
<212> TYPE: PRT
<213> ORGANISM: Streptomyces coelicolor A3

<400> SEQUENCE: 2

```
Leu Thr Thr Gly Gly Leu Val Gln Pro Ala Val Gln Asn Pro Ser Asp
1               5                   10                  15

Pro Asn Arg Asn Ile Leu Phe Asn Trp Ser Glu Tyr Thr Leu Asn Asp
            20                  25                  30

Gly Gly Leu Trp Leu Asn Ser Thr Gln Val Asp Met Phe Ser Ala Pro
        35                  40                  45

Tyr Thr Val Gly Val Gln Arg Ala Asp Gly Gly Val Thr Ser Ala Gly
    50                  55                  60

Gln Leu Lys
65
```

<210> SEQ ID NO 3
<211> LENGTH: 72
<212> TYPE: PRT
<213> ORGANISM: Streptomyces coelicolor A3

<400> SEQUENCE: 3

```
Gly Val Phe Asp Ala Leu Arg Ala Gln Pro Gly Trp Gly Gly Leu Ile
1               5                   10                  15

Gln Thr Arg Pro Asp Gly Thr Val Leu Arg Ala Leu Ala Pro Leu Tyr
            20                  25                  30

Gly Val Glu Thr Gly Ala Leu Pro Ala Ser Val Met Asp Asp Tyr Ile
        35                  40                  45

Asn Arg Val Trp Gln Lys Tyr Thr Thr Thr Leu Thr Val Thr Pro
    50                  55                  60

Phe Gly Asp Arg Pro Asp Thr Lys
65                  70
```

<210> SEQ ID NO 4
<211> LENGTH: 42
<212> TYPE: PRT
<213> ORGANISM: Streptomyces coelicolor A3

<400> SEQUENCE: 4

```
Val Ser Gly Asn Val Met Asn Phe Thr Asn Thr Ser Gly Ala Val Val
1               5                   10                  15

Thr Ser Phe Gln Lys Pro Asp Ala Ser Ser Val Phe Gly Cys His Arg
            20                  25                  30

Leu Leu Asp Ala Pro Asn Asp Gln Val Arg
        35                  40
```

<210> SEQ ID NO 5
<211> LENGTH: 78
<212> TYPE: PRT
<213> ORGANISM: Streptomyces coelicolor A3

<400> SEQUENCE: 5

```
Thr Leu Cys Ala Gly Phe Asn Arg Ser Thr Leu Leu Ser Asn Pro Asn
1               5                   10                  15

Gln Pro Asp Pro Ser Ala Ala Asn Phe Tyr Arg Asp Pro Val Thr Asn
            20                  25                  30
```

```
His Tyr Ala Arg Ile Ile His Glu Arg Met Ala Asp Gly Lys Ala Tyr
            35                  40                  45

Ala Phe Ala Phe Asp Asp Val Gly Asn His Glu Ser Leu Val His Asp
 50                  55                  60

Gly Asn Pro Ala Glu Ala Arg Leu Thr Leu Ala Pro Leu Asp
 65                  70                  75

<210> SEQ ID NO 6
<211> LENGTH: 398
<212> TYPE: PRT
<213> ORGANISM: Streptomyces coelicolor A3

<400> SEQUENCE: 6

Met Leu Ser Arg Leu Arg His Arg Leu Leu Ala Val Ala Ala Ala Ala
 1               5                  10                  15

Gly Leu Thr Gly Ala Leu Leu Ser Phe Gly Ala Ala Pro Pro Ala Asp
            20                  25                  30

Ala Ala Val Pro Ala Thr Ile Pro Leu Lys Ile Thr Asn Asn Ser Ala
        35                  40                  45

Arg Gly Asp Ala Val His Ile Tyr Asn Leu Gly Thr Ser Leu Thr Thr
 50                  55                  60

Gly Gln Gln Gly Trp Ala Asp Glu Asn Gly Thr Phe His Ala Trp Pro
 65                  70                  75                  80

Ala Gly Gly Asn Pro Pro Thr Pro Ala Pro Asp Ala Ser Ile Pro Gly
                85                  90                  95

Pro Ala Ala Gly Gln Thr Lys Thr Ile Arg Ile Pro Lys Leu Ser Gly
            100                 105                 110

Arg Ile Tyr Phe Ser Tyr Gly Gln Lys Leu Asp Phe Arg Leu Thr Thr
            115                 120                 125

Gly Gly Leu Val Gln Pro Ala Val Gln Asn Pro Ser Asp Pro Asn Arg
130                 135                 140

Asn Ile Leu Phe Asn Trp Ser Glu Tyr Thr Leu Asn Asp Gly Gly Leu
145                 150                 155                 160

Trp Leu Asn Ser Thr Gln Val Asp Met Phe Ser Ala Pro Tyr Thr Val
                165                 170                 175

Gly Val Gln Arg Ala Asp Gly Val Thr Ser Ala Gly Gln Leu Lys
            180                 185                 190

Ala Gly Gly Tyr Arg Gly Val Phe Asp Ala Leu Arg Ala Gln Pro Gly
            195                 200                 205

Trp Gly Gly Leu Ile Gln Thr Arg Pro Asp Gly Thr Val Leu Arg Ala
        210                 215                 220

Leu Ala Pro Leu Tyr Gly Val Glu Thr Gly Ala Leu Pro Ala Ser Val
225                 230                 235                 240

Met Asp Asp Tyr Ile Asn Arg Val Trp Gln Lys Tyr Thr Thr Thr Thr
                245                 250                 255

Leu Thr Val Thr Pro Phe Gly Asp Arg Pro Asp Thr Lys Tyr Phe Gly
            260                 265                 270

Arg Val Ser Gly Asn Val Met Asn Phe Thr Asn Thr Ser Gly Ala Val
            275                 280                 285

Val Thr Ser Phe Gln Lys Pro Asp Ala Ser Ser Val Phe Gly Cys His
        290                 295                 300

Arg Leu Leu Asp Ala Pro Asn Asp Gln Val Arg Gly Pro Ile Ser Arg
305                 310                 315                 320

Thr Leu Cys Ala Gly Phe Asn Arg Ser Thr Leu Leu Ser Asn Pro Asn
```

```
                325                 330                 335
Gln Pro Asp Pro Ser Ala Ala Asn Phe Tyr Arg Asp Pro Val Thr Asn
            340                 345                 350

His Tyr Ala Arg Ile Ile His Glu Arg Met Ala Asp Gly Lys Ala Tyr
            355                 360                 365

Ala Phe Ala Phe Asp Asp Val Gly Asn His Glu Ser Leu Val His Asp
            370                 375                 380

Gly Asn Pro Ala Glu Ala Arg Leu Thr Leu Ala Pro Leu Asp
385                 390                 395

<210> SEQ ID NO 7
<211> LENGTH: 401
<212> TYPE: PRT
<213> ORGANISM: Streptomyces matensis DIC-108

<400> SEQUENCE: 7

Met Leu Arg Thr Leu Arg Arg Val Thr Ala Val Ala Leu Gly Leu
1               5                   10                  15

Ala Thr Ala Leu Gly Gly Gly Trp Leu Ala Ala Gly Val Pro Ser Pro
            20                  25                  30

Ala His Ala Ala Val Pro Ala Thr Ile Pro Leu Thr Ile Thr Asn Asn
            35                  40                  45

Ser Gly Arg Ala Glu Gln Ile His Ile Tyr Asn Leu Gly Thr Glu Leu
50                  55                  60

Ser Ser Gly Arg Gln Gly Trp Ala Asp Ala Ser Gly Ala Phe His Pro
65                  70                  75                  80

Trp Pro Ala Gly Gly Asn Pro Thr Pro Ala Pro Asp Ala Ser Ile
                85                  90                  95

Pro Gly Pro Ala Pro Gly Arg Ser Thr Thr Ile Gln Ile Pro Lys Phe
            100                 105                 110

Ser Gly Arg Ile Tyr Phe Ser Tyr Gly Arg Lys Met Glu Phe Arg Leu
            115                 120                 125

Thr Thr Gly Gly Leu Val Gln Pro Ala Val Gln Asn Pro Thr Asp Pro
    130                 135                 140

Asn Arg Asp Ile Leu Phe Asn Trp Ser Glu Tyr Thr Leu Asn Asp Ser
145                 150                 155                 160

Gly Leu Trp Ile Asn Ser Thr Gln Val Asp Met Phe Ser Ala Pro Tyr
                165                 170                 175

Thr Val Gly Val Arg Arg Gly Asp Gly Thr Thr Leu Ser Thr Gly Lys
            180                 185                 190

Leu Arg Pro Gly Gly Tyr Asn Gly Val Phe Asn Ala Leu Arg Gly Gln
            195                 200                 205

Ser Gly Gly Trp Ala Asn Leu Ile Gln Thr Arg Ser Asp Gly Thr Val
    210                 215                 220

Leu Arg Ala Leu Ser Pro Leu Tyr Gly Val Glu Thr Gly Ala Leu Pro
225                 230                 235                 240

Ala Ser Val Met Asp Asp Tyr Ile Asn Arg Val Trp Asn Lys Tyr Thr
                245                 250                 255

Gly Thr Asp Leu Ile Val Thr Pro Phe Ala Asp Arg Pro Asp Val Arg
            260                 265                 270

Tyr Thr Gly Arg Val Ser Gly Val Leu Arg Phe Thr Asp Gly Ser
            275                 280                 285

Gly Ala Val Val Thr Thr Phe Gln Lys Pro Asp Ala Ser Ser Val Phe
    290                 295                 300
```

-continued

```
Gly Cys His Arg Leu Leu Asp Ala Pro Asn Asp Gln Val Arg Gly Pro
305                 310                 315                 320

Ile Ser Arg Thr Leu Cys Ala Gly Phe Asn Arg Thr Thr Leu Leu Ala
                325                 330                 335

Asn Pro His Gln Pro Asp Arg Ser Ala Ala Gly Phe Tyr Gln Glu Pro
            340                 345                 350

Val Thr Asn His Tyr Ala Arg Ile Ile His Ala His Met Ala Asp Gly
        355                 360                 365

Lys Ala Tyr Gly Phe Ala Phe Asp Asp Val Gly His His Glu Ser Leu
    370                 375                 380

Val His Asp Gly Asp Pro Arg Gly Ala Ser Leu Thr Leu Asp Pro Phe
385                 390                 395                 400

Asp
```

PROCESS FOR THE TREATMENT OF YEAST CELL WALLS WITH A LAMINARIPENTAOSE PRODUCING BETA-1,3-GLUCANASE

CROSS REFERENCE TO RELATED APPLICATIONS

This application is a § 371 National Stage Application of PCT/EP2015/055986, filed Mar. 20, 2015, which claims priority to EP14161040.2, filed Mar. 21, 2014.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2919208-393000_ST25.txt" created on 19 Sep. 2016, and 10000 bytes in size) is submitted concurrently with the instant application, and the entire contents of the Sequence Listing are incorporated herein by reference.

FIELD OF THE INVENTION

The present invention relates to a process for the treatment of a composition comprising yeast cell walls comprising β-1,3-glucans, the process comprising contacting said composition with a laminaripentaose-producing-β-1,3-glucanase.

BACKGROUND OF THE INVENTION

β-Glucans are a family of polysaccharides that is heterogeneous with respect to size, solubility and molecular structure. β-Glucans are polymers of glucose and the linkages can be 1,3, 1,4 and 1,6. The glucose chains in the β-glucan polymer can be linear or branched, with one type of linkages (e.g. 1,3) or a mixture of two or more (e.g. 1,3-1,4 or 1,3-1,6). The structure of the β-glucan highly influences the physical and chemical properties.

The most well-known polysaccharides made up of glucose are starch and cellulose. Starch is composed of amylose which is a linear polysaccharide with α-1,4 linkages and amylopectin which is a polysaccharide with α-1,4 linkages and branches having α-1,6 linkages. Cellulose is a linear β-glucan with β-1,4 linkages only.

Other well-known polysaccharides are the insoluble β-1,3 glucans pachyman and curdlan. Pachyman is a β-1,3-glucan derived from the sclerotia of Poria cocos (a *Basidiomycetes* sp.) and curdlan is produced by *Alcaligenes faecalis* var. *myxogenes*10C3K. Laminarin is a storage glucan found in brown algae and is a linear polysaccharide made up of a 1,3-glucan with 1,6 linkages. The ratio 1,3 to 1,6 is 3:1 (Wikipedia-wikipedia.org/wiki/Laminarin).

The β-glucans oat and barley are the two main cereals in terms of industrial supply of β-glucans. Oat β-glucan is water soluble and extensively studied for its health effect. The fibre is built of β-1,3 and β-1,4 linkages. Barley glucan contains the same linkages and is also water soluble.

The structure of yeast β-glucan is different from the cereal β-glucan and that results in different characteristics. Instead of chains of 1,3 and 1,4 linked glucose units, yeast β-glucan is composed of 1,3 and 1,6 linked monomers. The yeast glucan is found primarily in the yeast cell wall. The yeast cell wall contributes to 15-30% of the total dry weight of the cell.

The main components of the yeast cell wall are polysaccharides, protein and some chitin. The polysaccharides can be divided in β-glucans and mannans, composed of mannose monomers. The build-up of the cell wall is organized in layers. Roughly, one can divide the wall in three layers (Klis, F. M., *Cell Wall Assembly in Yeast*, Yeast 10, 851-869, 1994). The first layer is the surface of the cell and is composed mainly of mannoprotein. Below the first layer there is an inner layer between the surface and the plasma membrane and which consists of two layers. The inner layer closest to the plasma membrane is a fibrillar layer formed by β-1,3-glucan and the outer layer linking the inner layer and the surface is a more amorphous layer and is enriched in β-1,6-glucan chains to form a network. These components are cross-linked in various ways to form higher-order complexes. Covalent linkages are present between each of these components. The β-1,3-glucan is organized in helices, formed of either 1 or 3 chains of β-glucan. There are only a few branching points (β-1,6-linkage) in the network. The helices further reduce the solubility of the poorly water-soluble glucan. A small amount of chitin is also present which contributes to the insolubility of the fibres.

For the degradation of the various polysaccharides that occur in nature, many different enzymes have been identified. These so-called glycosidases or glycoside hydrolases (EC 3.2.1.x) form a large group of enzymes catalysing the hydrolysis of glycosidic bonds in oligo and polysaccharides. On cazy.org a continuously updated database can be found with all carbohydrate-active enzymes which are now categorized into 131 glycoside hydrolase families-see Cantarel BL, Coutinho PM, Rancurel C, Bernard T, Lombard V, Henrissat B (2009) The Carbohydrate-Active EnZymes database (CAZy): an expert resource for Glycogenomics. Nucleic Acids Res 37:D233-238 [PMID: 18838391].

Enzymatic degradation of yeast cells and yeast cell walls is being investigated already for a long time. Lytic enzymes are produced by bacteria, mycobacteria, streptomycetes and moulds. Several commercially available enzyme products (often containing a mixture of enzyme activities) are widely used for yeast genetics, to fuse or transform yeast cells and to generate protoplasts. The enzyme product Zymolyase® from Amsbio and purified from culture liquid of *Arthrobacter luteus*, contains a β-1,3-glucan-laminaripentaohydrolase as essential activity. Glucanex® from Novozymes is another product used to make yeast protoplasts, as well as Lyticase from Sigma. All three products contain other activities in addition to a glucanase such as protease and mannanase activity. In more detail these products do not only perform endo-hydrolysis of glucan but also exo-hydrolysis resulting in complete breakdown of the glucan into oligosaccharides and glucose.

A laminaripentaose-producing glucanase (LPHase) is a β-1,3-glucanase that liberates laminaripentaose as the major product from polysaccharides such as laminarin, pachyman or curdlan. Vrsanská et al (1977, Zeitschrift für Allgemeine Mikrobiologie, 17 (6), 465-480) have shown that a laminaripentaose-producing glucanase (glucanase I) from *Arthrobacter* GJM-1 is one of the enzymes of the yeast lytic system. Incubation of isolated yeast cell walls with glucanase I results in complete solubilisation of the yeast cell walls with the formation of only laminaripentaose.

In JP6192589 (1986—Dainippon Ink & Chemicals), a laminaripentaose-producing-β-1,3-glucanase (LPHase) of *Streptomyces matensis* DIC-108 is disclosed. The enzyme is used in a process to produce laminaripentaose from the polysaccharides curdlan, pachyman and/or laminarin. The production of the glucanase of *Streptomyces matensis* DIC-108 is disclosed in JP8173153. JP9262090 and Nakabayashi et al (1998—J.Ferm.Bioeng. 85(5), 459-464)) disclose the cloning and sequencing of the gene encoding the glucanase of *Streptomyces matensis* DIC-108. The authors also derived the amino acid sequence from the gene. The LPHase of *Streptomyces matensis* DIC-108 appears to be a unique enzyme since it shows only some amino acid sequence similarity (~60%) with two other β-1,3-glucanases from *Arthrobacter* sp.YCWD3 and *Oerskovia xanthineolytica* respectively which were 99% identical to each other on protein level (Shen et al. (1991) J. Biol. Chem 266(2) pp. 1058-1063 and references cited therein). The crystal structure of the LPHase was solved at 1.62 Å resolution and it turned out that the LPHase belongs to the glycoside hydrolase family 64 (Wu et al. J. Biol. Chem. 284 (39), 26708-26715 *"Structure, Mechanistic Action, and Essential Residues of a GH-64 Enzyme, Laminaripentaose-producing β-1, 3-Glucanase"*). In a recent study, Shresta et al determined the essential amino acids in the enzyme for catalysis (Protein Engineering, Design & Selection vol. 24 no. 8 pp. 617-625, 2011—*Characterization and identification of essential residues of the glycoside hydrolase family* 64 *laminaripentaose-producing-β-1,3-glucanase*).

Intact β-glucans (as part of dietary fibre) have interesting health properties, such as stimulation of the immune system in mammals. β-glucans are not digested by mammalian enzymes when orally administered and are taken up in the small intestine where it stimulates mucosal and system immunity by activating both innate and adaptive immunities. First major reported function of β-glucans was antitumor activity. Later reported biological activities include antifungal, anti-infection, radioprotective, cholesterol reduction and postprandial glucose metabolic activities.

The potency of the biological activities of water-soluble and particulate β-glucans is controversial, however it is recently reported that particulate β-glucans have stronger immunostimulating activities than water soluble β-glucans. Further, complete degradation of the glucans of yeast cell walls, either by enzyme mixtures yielding glucose and oligosaccharides or by a laminaripentaose-producing glucanase yielding laminaripentaose, has the disadvantage of the loss of the health properties.

The present inventors have found that intact β-glucans still present in the yeast cell wall matrix have only a limited bioavailability to the mammals when digested in the gastrointestinal tract. It is therefore a long felt need to, on the one hand increase the bioavailability of the β-glucans in the yeast cell wall and, on the other hand to preserve as much as possible the health properties such as the immune system stimulation. The present invention provides a process whereby β-glucans in yeast cell walls are only partially degraded by a laminaripentaose-producing-β-1,3-glucanase thus increasing on the one hand the bioavailability of the β-glucans and preserving on the other hand health properties such as the immune system stimulation.

BRIEF DESCRIPTION OF THE DRAWINGS

FIGS. 1-9 depict embodiments as described herein.

DETAILED DESCRIPTION OF A PREFERRED EMBODIMENT

Figure 4:
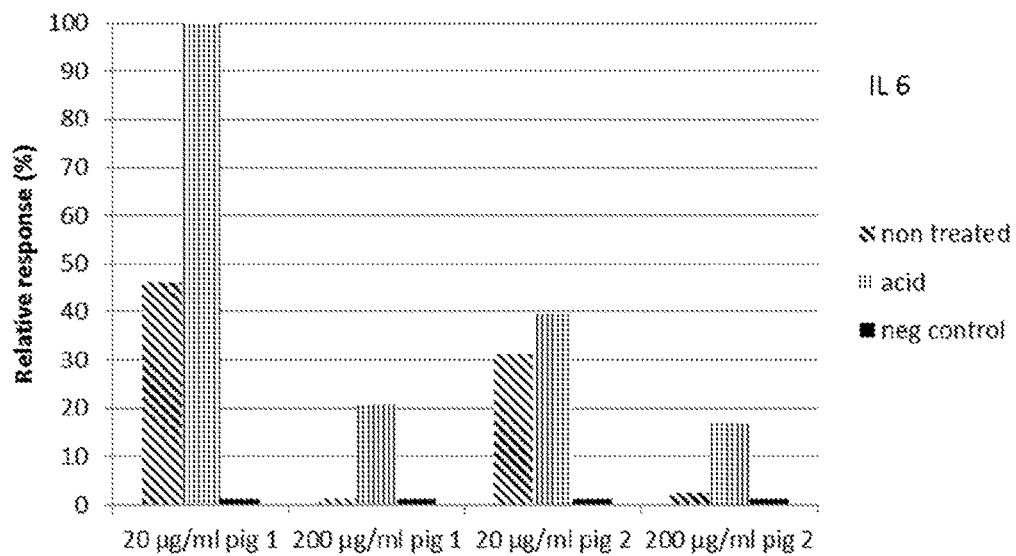

In a first aspect the invention provides a process for the treatment of a composition comprising yeast cell walls comprising β-1,3-glucans, or comprising β-glucans, which are insoluble when extracted with water and partially soluble when extracted with DMSO, the process comprising contacting said composition with laminaripentaose-producing-β-1,3-glucanase and inactivating the laminaripentaose-producing-β-1,3-glucanase to result in a composition comprising yeast cell walls wherein the β-1,3-glucans, or β-glucans, have an improved solubility in DMSO and the ratio of total β-glucans soluble in DMSO compared to water is greater than or equal to 2.

The advantage of the process of the invention is that by improving the DMSO-solubility of the β-glucans present in the yeast cell walls, the bioavailability is improved which results in an improved animal health when yeast cell walls treated according to the process of the invention are fed to animals. Therefore it is surprisingly shown by the present inventors that the degree of DMSO solubility in combination with the ratio of β-glucans soluble in DMSO compared with water is predictive for the bioavailability of the β-glucans present in the yeast cell wall. A laminaripentaose-producing-β-1,3-glucanase is defined herein as a glucanase that liberates laminaripentaose as the predominant product from polysaccharides such as laminarin, pachyman or curdlan as well as from the glucans present in the yeast cell wall—see for instance Nakabayashi et al. (1998). The laminaripentaose-producing-β-1,3-glucanase differs from other β-1,3-glucanases such as laminarinase since these β-1,3-glucanases produce various oligosaccharides as products.

Partially soluble when extracted with DMSO as used in the present context is defined as <15% of the total β-glucans present in the yeast cell wall is soluble in DMSO. An improved solubility in DMSO as used in the present context is defined as more than 15% of the total β-glucans present in the yeast cell wall are soluble in DMSO.

β-Glucans, as used in the present context, are defined as polysaccharides of D-glucose monomers linked by β-glycosidic bonds, comprising at least 10 D-glucose monomers.

Contacting said composition with laminaripentaose-producing-β-1,3-glucanase, as used in the present context, is preferably contacting or incubating said composition with laminaripentaose-producing-β-1,3-glucanase for a time period which is sufficient to result in a composition comprising yeast cell walls wherein the β-1,3-glucans, or β-glucans, have an improved solubility in DMSO and the ratio of total β-glucans soluble in DMSO compared to water is greater than or equal to 2.

In a preferred embodiment, the present invention relates to a process for the treatment of a composition comprising yeast cell walls comprising β-1,3-glucans which are insoluble when extracted with water and partially soluble (<15% of the β-glucans present in the yeast cell wall) when extracted with DMSO, the process comprising contacting said composition with laminaripentaose-producing-β-1,3-glucanase resulting in a composition comprising yeast cell walls wherein the β-1,3-glucans have an improved solubility in DMSO (more than 15% of the β-glucans present in the yeast cell wall are soluble in DMSO) and the ratio of glucans soluble in DMSO compared to water is greater than or equal to 2. Preferably this process is followed by inactivating the laminaripentaose-producing-β-1,3-glucanase to avoid the formation of laminaripentaose.

Preferably, the present process comprises contacting said composition with laminaripentaose-producing-β-1,3-glucanase and inactivating of the laminaripentaose-producing-β-1,3-glucanase to result in a composition comprising yeast cell walls wherein the β-1,3-glucans have an improved solubility in DMSO (more than 15% of the β-glucans present in the yeast cell wall are soluble in DMSO) and the ratio of β-glucans soluble in DMSO compared to water is greater than or equal to 2, wherein the amount of laminaripentaose produced by the laminaripentaose-producing-β-1, 3-glucanase is less than 30%, more preferably less than 20%, most preferably less than 10% (w/w) or less than 7.5% (w/w) of the total glucose units present in the composition.

In the present method, the degree of hydrolysis of β-glucans is such that the solubility of the β-glucans in DMSO is improved, however wherein the β-glucans are not, or not substantially, degraded into sugars such as laminaripentaose. Preferably, in the present process the present laminaripentaose-producing-β-1,3-glucanase is inactivated before glucose oligomers such as laminaripentaose is produced. The present inventors found that a partial hydrolysis of β-glucans increases the beneficial health properties such as immune system stimulation.

In a preferred embodiment, the present step of inactivating the laminaripentaose-producing-β-1,3-glucanase comprises heating the present resulting composition to a temperature above 70° C. for a time sufficient to inactivate the laminaripentaose-producing-β-1,3-glucanase. More preferably the resulting composition is heated to a temperature above 80° C., more preferably above 85° C., even more preferably above 90° C. or 95° C., most preferably above 100° C., for a time sufficient to inactivate the laminaripentaose-producing-β-1,3-glucanase.

In a preferred embodiment, the present laminaripentaose-producing-β-1,3-glucanase is comprising an amino acid sequence selected from the group consisting of SEQ ID No. 1, SEQ ID No. 2, SEQ ID No. 3, SEQ ID No. 4, SEQ ID No. 5, SEQ ID No. 6 and SEQ ID No. 7 or an amino acid sequence 60% or more identical to these sequences.

Preferably, the process of the invention results in a composition comprising yeast cell walls wherein more than 20% or more than 25% of the β-glucans present in the yeast cell walls are soluble in DMSO, more preferably more than 30%, more preferably more than 35%, more preferably more than 40%, most preferably more than 45% of the β-glucans present in the yeast cell walls are soluble in DMSO.

At the same time, the ratio of β-glucans soluble in DMSO compared to water is greater than or equal to 2, preferably greater than or equal to 3, greater than or equal to 4, greater than or equal to 5, greater than or equal to 10, greater than or equal to 50, greater than or equal to 100, greater than or equal to 500, greater than or equal to 1,000, greater than or equal to 5,000, greater than or equal to 10,000.

Instead of the ratio of β-glucans soluble in DMSO compared to water also the inverse ratio can be used to define the invention. The ratio of β-glucans soluble in water compared to DMSO is less than or equal to 0.5, preferably less than or equal to ⅓, less than or equal to 0.25, less than or equal to 0.2, less than or equal to 0.1, less than or equal to 0.02, less than or equal to 0.01, less than or equal to 0.001, less than or equal to 0.0005. Most preferred the ratio of β-glucans soluble in water compared to DMSO is close to zero or zero.

In a preferred embodiment the laminaripentaose-producing-β-1,3-glucanase comprises the amino acid sequence of SEQ ID No. 1 or an amino acid sequence which is 60% or more, preferably 65% or more, preferably 70% or more, preferably 75% or more, preferably 85% or more, preferably 90% or more, preferably 95% or more identical to SEQ ID: No 1.

In another preferred embodiment the laminaripentaose-producing-β-1,3-glucanase comprises the amino acid sequence of SEQ ID No. 2 or an amino acid sequence which is 60% or more, preferably 65% or more, preferably 70% or more, preferably 75% or more, preferably 85% or more, preferably 90% or more, preferably 95% or more identical to SEQ ID: No 2.

In another preferred embodiment the laminaripentaose-producing-β-1,3-glucanase comprises the amino acid sequence of SEQ ID No. 3 or an amino acid sequence which is 60% or more, preferably 65% or more, preferably 70% or more, preferably 75% or more, preferably 85% or more, preferably 90% or more, preferably 95% or more identical to SEQ ID: No 3.

In another preferred embodiment the laminaripentaose-producing-β-1,3-glucanase comprises the amino acid sequence of SEQ ID No. 4 or an amino acid sequence which is 60% or more, preferably 65% or more, preferably 70% or more, preferably 75% or more, preferably 85% or more, preferably 90% or more, preferably 95% or more identical to SEQ ID: No 4.

In another preferred embodiment the laminaripentaose-producing-β-1,3-glucanase comprises the amino acid sequence of SEQ ID No. 5 or an amino acid sequence which is 60% or more, preferably 65% or more, preferably 70% or more, preferably 75% or more, preferably 85% or more, preferably 90% or more, preferably 95% or more identical to SEQ ID: No 5.

In another preferred embodiment the laminaripentaose-producing-β-1,3-glucanase comprises two or more of the amino acid sequences of the group consisting of SEQ ID No. 1, SEQ ID No. 2, SEQ ID No. 3, SEQ ID No. 4, SEQ ID No. 5 or an amino acid sequence 60% or more identical to these sequences. Preferred embodiments are the β-1,3-glucanases comprising the following combinations of the amino acid sequences: SEQ ID No: 1+2, SEQ ID No: 1+3, SEQ ID No: 1+4, SEQ ID No: 1+5, SEQ ID No: 2+3, SEQ ID No: 2+4, SEQ ID No: 2+5, SEQ ID No: 3+4, SEQ ID No: 3+5, SEQ ID No: 4+5, SEQ ID No: 1+2+3, SEQ ID No: 1+2+4, SEQ ID No: 1+2+5, SEQ ID No: 1+3+4, SEQ ID No: 1+3+5, SEQ ID No: 2+3+4, SEQ ID No: 2+3+5, SEQ ID No: 3+4+5, SEQ ID No: 1+2+3+4, SEQ ID No: 2+3+4+5, SEQ ID No: 1+2+3+4+5.

Another preferred embodiment is the laminaripentaose-producing-β-1,3-glucanase from *Streptomyces coelicolor* A3 having the amino acid sequence depicted in SEQ ID No. 6 or in FIG. 2, or an amino acid sequence which is 60% or more, preferably 65% or more, preferably 70% or more, preferably 75% or more, preferably 85% or more, preferably 90% or more, preferably 95% or more identical to SEQ ID: No 6 or FIG. 2.

A further preferred embodiment is the laminaripentaose-producing-β-1,3-glucanase from *Streptomyces matensis* DIC-108 having the amino acid sequence depicted in SEQ ID No. 7 or in FIG. 3, or an amino acid sequence which is 60% or more, preferably 65% or more, preferably 70% or more, preferably 75% or more, preferably 85% or more, preferably 90% or more, preferably 95% or more identical to SEQ ID: No 7 or FIG. 3.

The identity between the two aligned sequences is defined as the number of corresponding positions in the alignment showing an identical amino acid in both sequences divided by the total length of the alignment after subtraction of the total number of gaps in the alignment. The identity defined as herein can be obtained from the computer program NEEDLE by using the NOBRIEF option and is labelled in the output of the program as "longest-identity". For purposes of the invention the level of identity (homology) between two sequences (amino acid or nucleotide) is calculated according to the definition of "longest-identity" as can be carried out by using NEEDLE (NEEDLE program from the EMBOSS package - version 2.8.0 or higher, EMBOSS: The European Molecular Biology Open Software Suite (2000) Rice, P. Longden, 1. and Bleasby, A. Trends in Genetics 16, (6) pp276-277 emboss.bioinformatics.nl).

The process of the invention is preferably carried out at a pH and at temperatures where the laminaripentaose-producing-β-1,3-glucanase as defined herein before is capable of catalysing the process of the invention and treating the glucans as defined hereinbefore. The pH is preferably 2 or higher, more preferably 3 or higher, more preferably 4 or higher and most preferably 5 or higher while at the same time the pH is preferably 9 or lower, preferably 8 or lower preferably 7 and most preferably 6 or lower. Preferred pH ranges are between 2 and 9, more preferably between 3 and 8, more preferably between 4 and 7 and most preferably between 5 and 6.

The temperature during contacting the present composition with the laminaripentaose-producing-β-1,3-glucanase is preferably 20° C. or higher, more preferably 30° C. or higher, more preferably 40° C. or higher and most preferably 50° C. or higher while at the same time temperature is preferably 90° C. or lower, more preferably 80° C. or lower, more preferably 70° C. or lower and most preferably 60° C. or lower. Preferred temperature ranges are between 20° C. and 90° C., more preferably between 30° C. and 80° C., more preferably between 40° C. and 70° C. and most preferably between 50° C. and 60° C.

It is generally known in the art that an optimal pH and temperature for an enzyme catalysed reaction and therefore also for the process of the invention are dependent on the type of laminaripentaose-producing-β-1,3-glucanase used. The time of the reaction can be easily determined by the skilled person and will be dependent on the yeast cell walls preparation, the type and dosage of the laminaripentaose-producing-β-1,3-glucanase used, the pH and the temperature as well as the desired treatment of the β-1,3-glucans in order to obtain the desired solubilisation in DMSO. The skilled person is very well capable, without undue burden, to determine the process conditions such that for a yeast cell wall preparation the DMSO-solubility of the glucans in the yeast cell walls is maximized while the water solubility of the glucans in the yeast cell walls in water with a pH of 6-7 is minimized.

In a second aspect, the invention provides a process for the treatment of a composition comprising yeast cell walls comprising β-1,3-glucans which are insoluble when extracted with water and partially soluble (<15% of the glucans present in the yeast cell wall) when extracted with DMSO, the process comprising incubating said composition at a pH in the range of 1-5 resulting in a composition comprising yeast cell walls wherein the β-1,3-glucans have an improved solubility in DMSO (more than 15% of the glucans present in the yeast cell wall are soluble in DMSO) and the ratio of glucans soluble in DMSO compared to water is greater than or equal to 2. Preferably the process of the second aspect of the invention is carried out at a pH in the range 1-4, more preferably in the range 1-3, most preferably in the range 2-3.

The temperature is preferably 40° C. or higher, more preferably 50° C. or higher, more preferably 60° C. or higher, more preferably 70° C. and most preferably 80° C. or higher while at the same time the temperature is preferably 125° C. or lower, more preferably 120° C. or lower, more preferably 115° C. or lower, more preferably 110° C. or lower, more preferably 105° C., most preferably 100° C. or lower. Preferred temperature ranges are 40-125° C., more preferably 50-120° C., more preferably 60-115° C., more preferably 70-110° C. and most preferably 80-100° C.

The time of the reaction can be easily determined by the skilled person and will be dependent on the yeast cell walls preparation, the pH and the temperature as well as the desired treatment of the β-1,3-glucans in order to obtain the desired solubilisation in DMSO. The skilled person is very well capable, without undue burden, to determine the process conditions such that for a yeast cell wall preparation the DMSO-solubility of the glucans in the yeast cell walls is maximized while the water solubility of the glucans in the yeast cell walls in water is minimized.

In a preferred embodiment, the temperature during incubation at a pH of 1-5, or preferably at pH 1-3 or at 2-3 is decreased to a temperature below 50° C., preferably below 40° C., more preferably below 30° C., even more preferably below 25° C. or 20° C., most preferably below 10° C. when the ratio of β-glucans soluble in DMSO compared to water is greater than or equal to 2 is achieved. The advantage of timely stopping the acid incubation is that the β-glucans preserve their biological beneficial properties since the β-glucans are not completely hydrolysed.

The composition comprising yeast cell walls which are used in the process of the first aspect as well as the second aspect of the invention may be of any origin. Yeast cell walls are commercially available from various suppliers, in particular from *Saccharomyces cerevisiae*. Yeast cell walls may be a side stream of a commercial yeast extract which is produced on an industrial scale. The yeast from which the yeast cell walls are derived may be any suitable yeast. Suitable yeasts are all food grade yeasts (see Bekatorou et al 2006, Food Technol. Biotechnol. 44 (3), 407-415) for instance yeasts from the genera *Saccharomyces, Kluyveromyces, Candida* and others. *Saccharomyces*, in particular *Saccharomyces cerevisiae* is often used for the production of yeast extract.

In a third aspect the invention provides a composition comprising yeast cell walls comprising β-1,3-glucans characterized in that more than 15% of the β-glucans are soluble in DMSO and the ratio of β-glucans soluble in DMSO compared to soluble in water is greater than or equal to 2. Preferably the composition is obtainable by the process of the first or second aspect of the invention. Preferably, the invention provides a composition comprising yeast cell walls comprising β-1,3-glucans wherein more than 25% of the β-glucans present in the yeast cell walls are soluble in DMSO, more preferably more than 30%, more preferably more than 35%, more preferably more than 40%, most preferably more than 45% of the β-glucans present in the yeast cell walls are soluble in DMSO. At the same time, the ratio of β-glucans soluble in DMSO compared to water is greater than or equal to 2, preferably greater than or equal to 3, greater than or equal to 4, greater than or equal to 5, greater than or equal to 10, greater than or equal to 50, greater than or equal to 100, greater than or equal to 500, greater than or equal to 1,000, greater than or equal to 5,000, greater than or equal to 10,000. Instead of the ratio of β-glucans soluble in DMSO compared to water also the inverse ratio can be used to define the invention. The ratio of β-glucans soluble in water compared to DMSO is less than or equal to 0.5, preferably less than or equal to ⅓, less than or equal to 0.25, less than or equal to 0.2, less than or equal to 0.1, less than or equal to 0.02, less than or equal to 0.01, less than or equal to 0.001, less than or equal to 0.0005. Most preferred the ratio of glucans soluble in water compared to DMSO is close to zero or zero.

Preferably, the present composition comprises less than 30%, more preferably less than 20%, most preferably less than 10% or less than 7.5% laminaripentaose in (w/w) of the total glucose units present in the composition. More preferably the present composition does not comprise laminaripentaose, or does not comprise substantial amounts of laminaripentaose. It is advantageous if no laminaripentaose is present because the amount of partially degraded β-glucans is higher, and thus the biological beneficial effects increase.

Further, the present invention relates to a starter feed comprising the present composition, which starter feed further comprises 10 to 30% (w/w) protein. Starter feeds are beneficial since they provide proper nutrition for growing animals like baby chickens. Usually a starter feed is fed to animals having the age of 0 to 10 weeks. Preferably such a starter feed comprises the composition of the present invention comprising DMSO soluble β-glucans, 10 to 20% (w/w) protein, 30 to 40% (w/w) starch, calcium and/or phosphor. The amount of the β-glucans present in the composition of the present invention in a starter feed is preferably within the range of 1 to 500 mg per kg starter feed, more preferably 1 to 200 mg per kg starter feed, most preferably 1 to 50 mg per kg starter feed. The present inventors found that using a starter feed of the present invention provides an improved feed conversion ratio and a reduced lethality.

Given the beneficial biological health properties of the present β-glucans, the invention relates, according to a fourth aspect, to the use of the present composition or starter feed of the second aspect of the invention and preferably obtainable by the process of the first or third aspect of the invention as a food or feed ingredient.

In a preferred embodiment, the present invention relates to the use of the present composition, or use of the present starter feed, for improving the feed conversion ratio of animals, preferably of farm animals, more preferably of pigs or chickens such as broiler chickens. The present inventors found that glucans having an increased solubility in DMSO provide beneficial effects for the growth of broiler chicken by lowering the feed conversion ratio. Further, the present inventors found that by feeding the present composition comprising glucans having an increased solubility in DMSO decreases the lethality in broiler chicken. Therefore, in preferred embodiment, the present invention relates to the use of the present composition for decreasing the lethality in broiler chicken, more preferably for decreasing the lethality in broiler chicken during the first 35 days of growth after birth.

According to another aspect, the present invention relates to the present composition comprising yeast cell walls comprising β-1,3-glucans characterized in that more than 15% of the β-1,3-glucans are soluble in DMSO and the ratio of β-1,3-glucans soluble in DMSO compared to soluble in water is greater than or equal to 2, for use as a medicament.

In a preferred embodiment, the present invention relates to the present composition comprising yeast cell walls comprising β-1,3-glucans characterized in that more than 15% of the β-1,3-glucans are soluble in DMSO and the ratio of β-1,3-glucans soluble in DMSO compared to soluble in water is greater than or equal to 2, for stimulating the growth of animals, and/or for stimulating the immune system in animals. Preferred animals are pigs or chicken such as broiler chicken. Preferably, the present invention relates to the present composition for increasing or to induce the IL-6 and IL-10 secretion in pigs. Preferably the present invention relates to the present composition for increasing or to induce IgM and IgG secretion, preferably for increasing or to induce IgM and/or IgG secretion in chickens.

In a further preferred embodiment, the present invention relates to the present composition for stimulating growth of animals and/or for stimulating the immune system of animals, wherein the composition is fed to animals for a time period of at most 15 or at most 10 weeks after birth, more preferably for a time period of at most 5 weeks after birth, more preferably for a time period of at most 3 weeks or at most 2 weeks after birth.

More preferably, the present composition for stimulating growth of animals and/or for stimulating the immune system of animals is added to a starter feed in an amount of 1 to 500 mg β-glucans per kg starter feed, more preferably 1 to 200 mg β-glucans per kg starter feed, most preferably 1 to 50 mg β-glucans per kg starter feed.

Figure Legends

Figure 5:
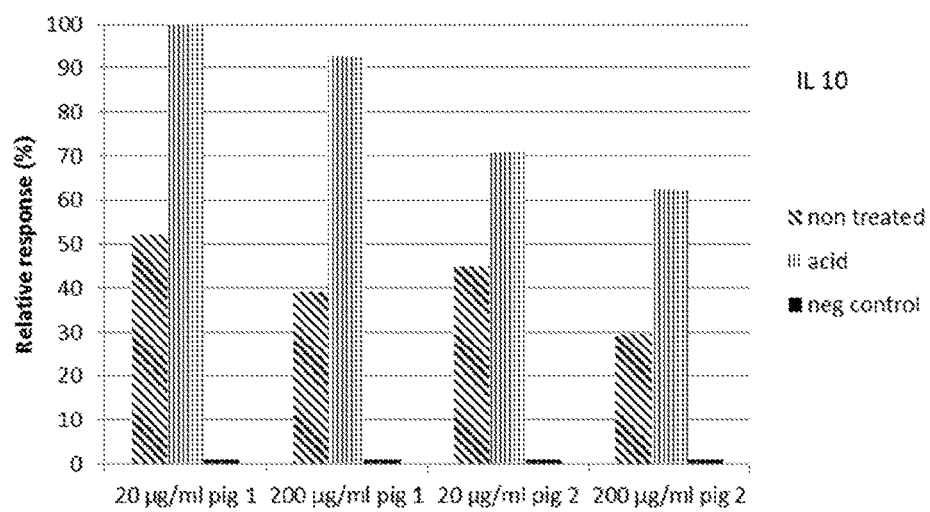
Figure 6:
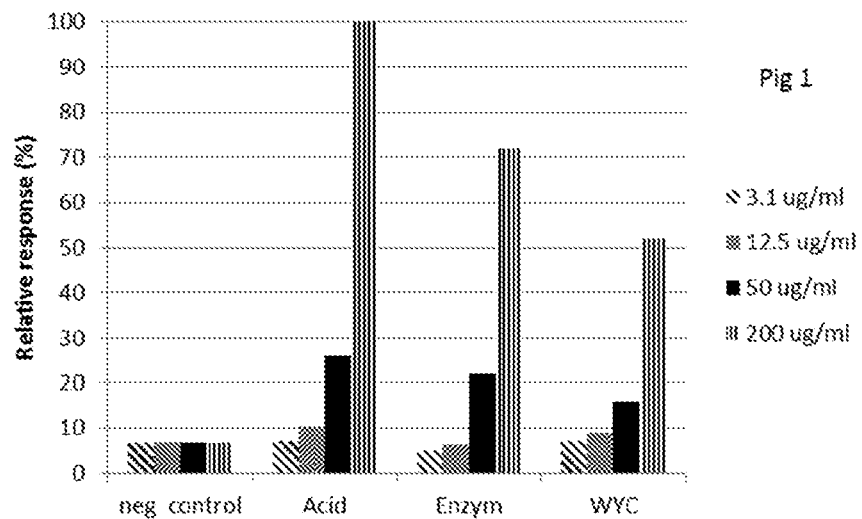
Figure 7:
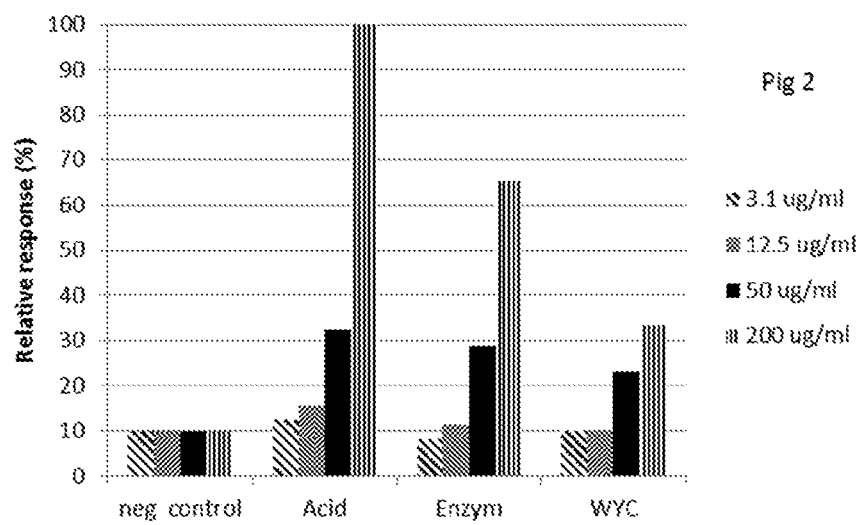
Figure 8:
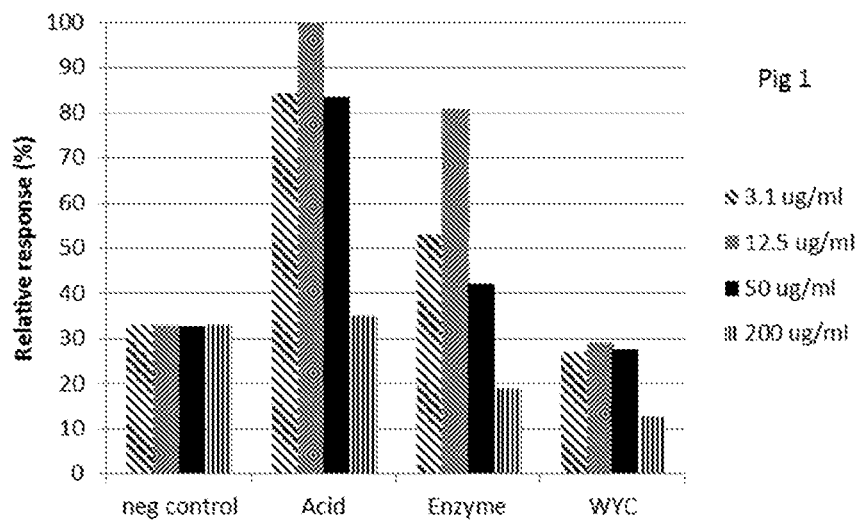

FIG. 1—NMR spectrum
1A—upper panel-NMR spectrum in $D_2O$. t=terminal units; 1,3=β-1,3-glucan; 1,6=β-1,6-glucan
1B—lower panel-NMR spectrum in DMSO. t=terminal units; 1,3=β-1,3-glucan; 1,6=β-1,6-glucan; b=branching units
For a further explanation see Materials and Methods under DMSO soluble glucan and water soluble glucan respectively.
FIG. 2—SEQ ID NO. 6; laminaripentaose-producing-β-1,3-glucanase from *Streptomyces coelicolor* A3.
FIG. 3—SEQ ID No. 7; laminaripentaose-producing-β-1,3-glucanase from *Streptomyces matensis* DIC-108.
FIG. 4—Production of IL 6 after stimulation with 20 or 200 μg/ml of β-glucans from non-treated yeast cell walls of Example 2 (non treated), acid treated yeast cell walls (acid) at pH 3 of Example 2, incubation 2 and a negative control (neg control). The relative response is calculated based on the maximum response obtained with the acid treated yeast cell walls at 20 μg/ml (pig 1).
FIG. 5—Production of IL 10 after stimulation with 20 or 200 μg/ml of β-glucans from non-treated yeast cell walls of Example 2 (non treated), acid treated yeast cell walls (acid) at pH 3 of Example 2, incubation 2 and a negative control (neg control). The relative response is calculated based on the maximum response obtained with the acid treated yeast cell walls at 20 μg/ml (pig 1).
FIG. 6—The relative ROS production of neutrophils isolated from a pig (pig 1), expressed relatively to the maximal value that was measured after addition of acid treated yeast cell walls at a dose of 200 μg/ml, for four different dosages of a negative control (neg control), acid treated cell wall (acid), enzyme treated cell walls (enzyme) and wheat yeast concentrate (WYC).
FIG. 7—The relative ROS production of neutrophils isolated from a pig (pig 2), expressed relatively to the maximal value that was measured after addition of acid treated yeast cell walls at a dose of 200 μg/ml, for four different dosages of a negative control (neg control), acid treated cell wall (acid), enzyme treated cell walls (enzyme) and wheat yeast concentrate (WYC).
FIG. 8—The relative ROS production of monocytes isolated from a pig (pig 1), expressed relatively to the maximal value that was measured after addition of the acid treated yeast cell walls at a dose of 12.5 μg/ml, for four different dosages of a negative control (neg control), acid treated cell wall (acid), enzyme treated cell walls (enzyme) and wheat yeast concentrate (WYC).

Figure 9:
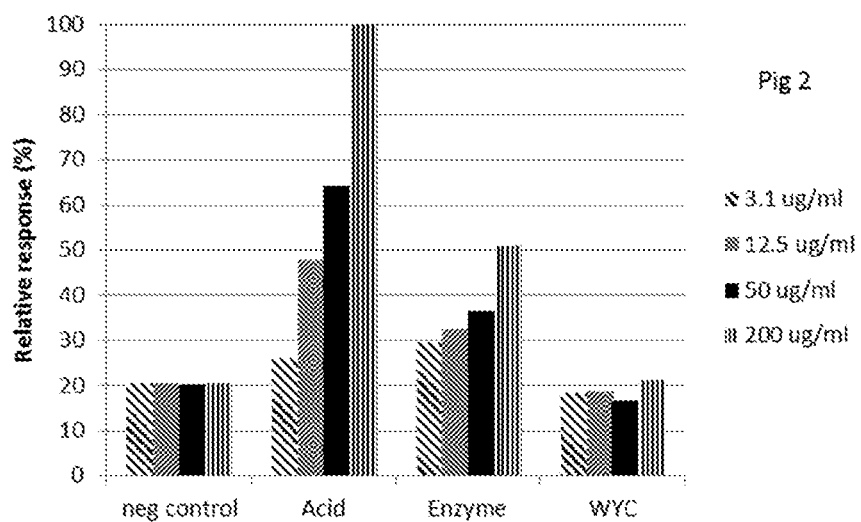

FIG. 9—The relative ROS production of monocytes isolated from a pig (pig 2), expressed relatively to the maximal value that was measured after addition of the acid treated yeast cell walls at a dose of 200 µg/ml, for four different dosages of a negative control (neg control), acid treated cell wall (acid), enzyme treated cell walls (enzyme) and wheat yeast concentrate (WYC).

Materials and Methods

Denazyme Gel-L1

Denazyme Gel-L1 Lot no T2 was obtained from Nagase ChemTeX Corporation (Kyoto, Japan). According to the technical datasheet of the manufacturer, Denazyme Gel-L1 is a purified liquid glucanase preparation produced by submerged fermentation of the genus Streptomyces. According to the enzyme assay of laminaripentaose-producing-β-1,3-glucanase described below, the activity of Denazyme Gel-L1 Lot no T2 is ~1300 units/ml.

Laminarinase

Laminarinase was purchased from Sigma-Aldrich (L9259). The powder was dissolved to give a solution of is ~1300 units/ml.

Enzyme Assay for Laminaripentaose-Producing-β-1,3-Glucanase Activity

Curdlan Solution—A 100 ml solution of 0.5% wt/vol curdlan (Sigma C7821, lot 042M4040V) was made dissolving the curdlan in 1M sodium acetate buffer pH-5 and incubating for 1 hour at room temperature (approximately 20° C.) followed by a 15 minute incubation at 60° C. under continuous stirring using a magnetic stir bar. To further homogenize the suspension, it was treated for 60 seconds at 9500 rpm with an IKA T-25 ultra-turrax type 525-25F (teeth stator 12, rotor 8).

Hoffman's Reagent—Dissolve in approximately 900 ml water in a 1 l volumetric flask: 1.17 g potassium hexacyanoferrate(III) (analytical reagent) followed by 19.5 g sodium carbonate anhydrous (analytical reagent). Make up to volume with water and mix. Always use a freshly prepared solution.

Enzyme Assay—2 ml of the curdlan solution was heated in a water bath at 37° C. after which 1 ml of a diluted (in 100 mM sodium acetate buffer pH 5) enzyme solution was added. The mixture was incubated for 30 minutes after which the reaction was stopped by adding 2 ml 1 M NaOH followed by adding 4 ml Hoffman's reagent. The mixture was incubated for 15 minutes in a boiling water bath. After cooling to room temperature, insoluble curdlan was removed by centrifugation and the optical density of the supernatant was measured at 420 nm. Blank samples are used for correcting the absorption of the corresponding sample; they are determined in the same way as described above for the samples, except that first stop reagent is added and then sample. A calibration curve with dilutions between 0.3 and 1.4 mM glucose was prepared to determine the concentration of reducing sugars in the assay mixture in the same way as described above for enzyme samples. Water instead of diluted glucose solutions were used as blanks for the calibration line.

The enzyme solution added to the assay mixture must have between approximately 0.25 to 0.5 units/ml in order to be in the linear range of the enzyme assay.

One unit of laminaripentaose-producing-β-1,3-glucanase is defined herein as the amount of enzyme necessary to liberate an amount of reducing sugars equivalent to 1 µmole glucose per minute under the conditions of the assay as described above (0.5% curdlan, pH=5, 37° C.).

Saeman Hydrolysis

Cell walls were hydrolysed according to a modified Saeman hydrolysis (J. F. Saeman, W. E. Moore, R. L. Mitchell, M. A. Millett (1954) Tappi, 37(8), 336-343). App 12 mg of isolated yeast cell walls were weighed accurately and 0.300 ml of 72% (w/w) $D_2SO_4$ were added to the sample. The sample was stored for 48 hours at 4° C. in a refrigerator (primary hydrolysis). Next, 1.700 ml of $D_2O$ was added and 1.000 ml of a stock solution of maleic acid in $D_2O$. After mixing well 0.500 ml of the solution was pipetted, and 0.500 ml of $D_2O$ was added. The insolubles were removed by centrifugation and the clear supernatant was transferred to an NMR tube. The NMR tube was placed in boiling water for 100 minutes (secondary hydrolysis).

NMR spectra were recorded on a Bruker AvanceIII 600 MHz NMR spectrometer, equipped with a 5 mm cryo probe. Sample temperature was 280K. Acquisition time was 2 sec and an interpulse delay of 30 sec was chosen. 16 scans were averaged and the spectrum was phased carefully and the baseline was adjusted. Signals of maleic acid (6.5 ppm), α- and β-glucose (5.22 and 4.62 ppm) and α- and β-mannose (5.18 and 4.90 ppm) were integrated, and the quantity of mannan and glucan were calculated according to quantitative NMR (qNMR), see equation 1:

$$P_x = \frac{A_x}{A_{st}} \times \frac{n_{st}}{n_x} \times \frac{MW_x}{MW_{st}} \times \frac{W_{st}}{W_x} \times P_{st}$$

$A_x$=Integral peak of product.
$A_{st}$=Integral of internal standard peak
$n_{st}$=number of protons corresponding to the internal standard peak
$n_x$=number of protons corresponding to the product peak
$MW_x$=molecular weight of product, 162 for glucose and mannose units
$MW_{st}$=molecular weight internal standard
$W_{st}$=Weight internal standard
$W_x$=Weight sample
$P_{st}$=purity internal standard A correction factor for degradation of monomeric glucose (0.984) and monomeric mannose (0.966) was used.

DMSO Soluble Glucan

App 100 mg of sample was weighed accurately (to within 0.01 mg). A stock solution of DMSO-d6 containing an accurately weighed amount of maleic acid was prepared and 1.000 ml of this solution was added to the cell walls. The suspension was placed in a water bath at 50° C. for 30 minutes. The insolubles were removed by centrifugation. 50 µl of $D_2O$ was added to the clear supernatant to ensure exchange of OH protons, and NMR spectra were recorded on a Bruker Avance III 600 MHz spectrometer, equipped with a 5 mm cryo probe. Sample temperature was 320K. Acquisition time was 1.7 sec and an interpulse delay of 10 sec was chosen. 32 scans were averaged, and after careful phasing and baseline adjustments the signals of β-(1,3) glucan at 4.57 ppm, β-(1,6) glucan at 4.31 ppm, terminal residues at 5.02 and 4.44 ppm, branching units at 4.50 and 4.42 ppm (see FIG. 1B) and of maleic acid at 6.1 ppm were integrated. The content of liberated glucan (sum of all types) was calculated from the integral ratios and the known molecular weights and sample weights by applying the standard qNMR method (equation 1).

The DMSO soluble glucans are reported on dry matter (w/w % on dm). The relative DMSO soluble glucan content is defined as the % of the total glucans and calculated according equation 2:

$$DMSO\ soluble\ glucans\ (Rel\ \%) = \frac{DMSO\ soluble\ glucans\ (\%\ on\ dm)}{Total\ glucans\ (\%\ on\ dm)} \times 100$$

Water Soluble Glucan

All samples (15 mg) were dissolved in 0.5 ml $D_2O$ and 0.5 ml $D_2O$ with 10.91 mg/ml malic acid, followed by adjusting the pH by adding 200 µl 1M phosphate buffer of pH 8.5. The resulting pH is in the range 6-7, depending on the for instance the batch of yeast cells.

Samples were centrifuged for 10 minutes and supernatant was analysed. Spectra were recorded at 280K. NMR spectra were recorded on a Bruker Avance III 600 MHz spectrometer, equipped with a 5 mm cryo probe. Sample temperature was 280K. Acquisition time was 2 sec and an interpulse delay of 30 sec was chosen. 16 scans were averaged. After careful phasing and baseline correction, the signal of maleic acid at 6.1 ppm was integrated. The amount of glucan was evaluated from the signal areas of β(1,3) glucan at 4.82-4.70 ppm, terminal residues at 5.23 and 4.67 ppm and β(1,6) glucan at 4.58-4.51 ppm. All integrals shown in FIG. 1A were added to obtain the sum of water soluble glucan. The content of water soluble glucan was calculated from the integral ratios and the known molecular weights and sample weights by applying standard qNMR methods (equation 1).

The water soluble glucans are reported on dry matter (w/w % on dm). The relative water soluble glucan content is defined as the % of the total glucans and calculated according equation 3:

$$Water\ soluble\ glucans\ (Rel\ \%) = \frac{Water\ soluble\ glucans\ (\%\ on\ dm)}{Total\ glucans\ (\%\ on\ dm)} \times 100$$

In-Vitro Assays
Reactive Oxygen Species (ROS) Production with Neutrophils or Monocytes The immunomodulating effect of β-glucans from untreated yeast cell walls, acid treated yeast cell walls, enzyme treated yeast cell walls and the wheat yeast concentrate (market reference) was tested on neutrophils and monocytes isolated from two pigs able to produce reactive oxygen species (ROS). The reactive oxygen species (ROS) production after addition of the samples to the cell medium at different concentrations, is a measure of the non-specific defence against pathogens. The quantity ROS was measured using a chemiluminisence assay as described by Donne et al., 2005, Vet. Microbiol. 107, 205-214. Hanks Balanced Salt Solution (HBSS) was used as a negative control. To test the reactive oxygen species production, the cells were stimulated with phorbol 12-myristate 13-acetate (PMA). The neutrophils or the monocytes were coated on the plastic surface of separate wells of a microtiter plate. After incubation for 2 h at 37° C. in a $CO_2$ atmosphere, the supernatant was removed and luminol was added. After 5 minutes a background measurement was done and the β-glucans were added in different concentrations, as well as the negative control. The ROS production was measured during 120 minutes. The ROS production was expressed as a relative response value related to the maximal value that was expressed as 100%.

Production of Pro-Inflammatory (Interleukin (IL)-6) and Anti-Inflammatory (IL-10) Cytokines Isolated peripheral blood mononuclear cells (PBMC's) (macrophages, monocytes, B and T cells) from 2 pigs were incubated in a medium including β-glucans from untreated yeast cell walls or acid treated yeast cell walls. The effect of two different concentrations of β-glucans (20 µg/ml and 200 µg/ml) on the cells is analysed by measurement of the IL-6 and IL-10 expression. The concentrations of IL-6 and IL-10 were measured using commercially available ELISA kits (R&D Systems Inc.; Minneapolis, Minn., USA) according to the manufacturers recommended protocols.

In-Vivo Study with Broiler Chickens

An in-vivo study with several groups of broiler chickens was performed to determine the average chicken weight (equation 4), the feed conversion ratio 1500 g (equation 5), the immuno response (Elisa) and lethality (equation 6) of broiler chickens. During the trial the chickens were fed with standard starter feed (control) and standard starter feed comprising β-glucans (Chemical composition Table 1). The starter feed comprising β-glucans consisted of the control starter feed with the addition of 50 mg β-glucans per kg feed. These β-glucans originated from a combination of β-glucans (25 mg) from standard wheat yeast concentrate and β-glucans (25 mg) from acid treated yeast cell walls. The starter feed comprising β-glucans was only fed during the start of the feed trial (initial 10 days). The feed trial was continued for 35 days. At the end of the feed trial (after 35 days) the broiler chicken weight increase and the consumed feed were determined to calculate the feed conversion ratio 1500 g (equation 5). The lethality was calculated based on the difference in viable broiler chickens at the start of the feed trial and at the end of the feed trial (equation 6). Blood samples were taken and the serum was analysed on the natural immune system response via ELISA (IgM and IgG concentrations).

Average Chicken Weight According Equation 4:

$$Average\ chicken\ weight\ (g) = \frac{Total\ meat\ weight\ (g)}{Amount\ of\ chickens_{end}}$$

The feed conversion ratio 1500 g (FCR 1500 g) is defined by each 25 g of the chicken weight above 1500 g, that reduces the feed conversion ratio with 0.01 and calculated according equation 5:

$$FCR\ 1500\ g = \frac{Total\ feed\ weight\ (kg)}{Total\ weight\ of\ meat\ (kg)} - \frac{(Avg.\ chicken\ weight\ (g) - 1500)}{(25 \times 100)}$$

Lethality According Equation 6:

$$Lethality\ (\%) = \frac{Amount\ of\ chickens_{start} - Amount\ of\ chickens_{end}}{Amount\ of\ chickens_{start}} \times 100$$

Broiler Chicken Standard Starter Feed Composition

The chemical composition of the broiler chicken standard starter feed (control) and starter feed comprising β-glucans applied during the initial 10 days of the in-vivo feed trial are presented in table 1:

TABLE 1

Chemical composition of broiler chicken composed feed

| | Standard starter feed (Control) | Starter feed comprising β-glucans |
|---|---|---|
| Dry matter (%) | 89.3 | 89.3 |
| Crude protein (g/kg) | 203 | 207 |
| Crude fat (g/kg) | 52 | 55 |
| Fibre (g/kg) | 35 | 33 |
| Ash (g/kg) | 52 | 51 |
| Starch (g/kg) | 364 | 362 |
| Glucose (g/kg) | 44 | 42 |
| Calcium (g/kg) | 8.0 | 7.6 |
| Phosphorus (g/kg) | 5.7 | 5.6 |
| Magnesium (g/kg) | 1.7 | 1.7 |
| Sodium (g/kg) | 1.5 | 1.4 |
| Potassium (g/kg) | 8.3 | 8.4 |
| Chlorine (g/kg) | 2.0 | 2.0 |

ELISA Assay

All blood plasma samples were analysed on the same day for antibodies against Keyhole Limpet Hemocyanin (KLH) by Enzyme-Linked Immunosorbent Assay (ELISA).

Microtiter plates (96 wells) were coated with KLH at a concentration of 4 µg/ml in a 0.1 M sodium carbonate buffer pH 9.6 for 1.5 hour at ambient temperature or overnight at refrigerated temperature. Microtiter plates were washed with excess of water and dried. Appropriate dilutions of the blood plasma samples were prepared in phosphate buffered saline (PBS) buffer with 0.5% horse serum and 0.05% Tween-20. Example: dilutions 1/40, 1/160, 1/640 etc. Pipette 100 µl of the prepared dilutions in the wells (n=10 or n=20) and add to each plate also the known standards. Incubate the microtiter plate for 1.5 hour at ambient temperature. Wash the plate with excess of water and dry the plate. Dilute conjugate (Chicken Ig G-Fc HRP or Chicken Ig M HRP) in diluting fluid: 1/40,000 or 1/20,000, and pipette 100 µl of the conjugate in each well. Incubate the microtiter plate for 1.5 hour at ambient temperature. Wash the plate with excess of water to remove unbound HRP labelled antibodies and dry. Finally 100 µl of the chromogenic substrate containing tetramethylbenzidin (TMB) is added to each well and incubated for 10 minutes. The reaction is stopped by the addition of 50 µl of 1.25 M sulphuric acid solution to each well. The plates were measured with an Elisa Reader at a wavelength of 450 nm. The data interpretation was based on the measured values of the different dilutions of each sample.

EXAMPLES

Example 1

Amino Acid Sequence of the Laminaripentaose-Producing-β-1,3-Glucanase Present in Denazyme Gel-L1.

1.1 Digestion of the Laminaripentaose-Producing-β-1,3-Glucanase Present in Denazyme Gel-L1 with Trypsin.

The protein present in Denazyme GEL-L1 was precipitated with TCA (trichloroacetic acid) by diluting it 1:1 with 20% TCA. The mixture was incubated for 30 minutes at 4° C. and the protein was collected by centrifugation. The protein pellet was washed with ice cold acetone, re-collected by centrifugation and dissolved in a small volume 50 mM sodium hydroxide. The protein solution was diluted 10-fold with 100 mM ammonium bicarbonate. Disulphide bridges were reduced by addition of 5 mM final concentration dithiothreithol and 30 minute incubation at 25° C. Cysteines were alkylated by addition of 5.5 mM final concentration iodoacetamide and 30 minute incubation at 25° C. in the dark. Alkylation was quenched by exposing the sample to light, prior to digestion with trypsin. Trypsin was added in a 1:100 molar ratio to the substrate and digestion was performed by incubation at 37° C. overnight.

1.2 LC-MS/MS Analysis and Protein Identification

The protein digest was analysed by LC-MS/MS and the resulting data were searched against the Uniprot database as described by Nitsche et al. BMC Genomics 2012, 13:380. The amino acid sequence of the laminaripentaose-producing-β-1,3-glucanase of *Streptomyces coelicolor* A3 (NCBI genbank accession number CAC_16439) was the best hit when the acquired MS and MS/MS data were matched against the Uniprot database.

Table 2 summarizes the molecular mass of the 20 peptides, their amino acid sequence (one letter code) as deduced from the NCBI genbank and the position of amino acids of the peptides in the amino acid sequence of the laminaripentaose-producing-β-1,3-glucanase of *Streptomyces coelicolor* A3. The 20 peptides show overlap. In total 5 unique peptides can be made from the 20 peptides—see Table 3. The five unique peptides have been included in the sequence listing as SEQ ID NO: 1 to 5 respectively.

Table 4 shows the amino acid sequence of the laminaripentaose-producing-β-1,3-glucanase of *Streptomyces coelicolor* A3 which was taken from the NCBI genbank (accession number CAC_16439). The underlined part of the amino acid sequence represents the signal sequence (33 amino acids) as was disclosed by Nakabayashi et al. (1998) for the homologous laminaripentaose-producing-β-1,3-glucanase of *Streptomyces matensis* DIC-108 (in J. Ferm. Bioeng. 85(5), 459-464 *"Structure of the Gene Encoding Laminaripentaose-Producing beta-1,3-glucanase (LPHase) of Streptomyces matensis DIC-108*). The highlighted peptides (grey background) are the 5 unique peptides found in the laminaripentaose-producing-β-1,3-glucanase isolated from the Denazyme GEL-L1. Based on the perfect fit of these 5 pepetides with the amino acid sequence of the *Streptomyces coelicolor* A3 beta-1,3-glucanase, it may be speculated that the laminaripentaose-producing-β-1,3-glucanase isolated from the Denazyme GEL-L1 has the same amino acid sequence as the *Streptomyces coelicolor* A3 beta-1,3-glucanase.

TABLE 2

Peptides obtained from the trypsin digest of Denazyme-L1.

| Mass | Peptide | Amino acid positions in the sequence of the beta-1,3-glucanase of *Streptomyces coelicolor* A3 |
|---|---|---|
| 1004.50 | IYFSYGQK | 114 - 121 |
| 1963.01 | LTTGGLVQPAVQNPSDPNR | 126 - 144 |
| 4134.98 | NILFNWSEYTLNDGGLWLNSTQVDMFSAPYTVGVQR | 145 - 180 |
| 1102.56 | ADGGVTSAGQLK | 181 - 192 |
| 2779.49 | GVFDALRAQPGWGGLIQTRPDGTVLR | 198 - 223 |
| 2021.08 | AQPGWGGLIQTRPDGTVLR | 205 - 223 |
| 2535.27 | ALAPLYGVETGALPASVMDDYINR | 224 - 247 |
| 3076.57 | ALAPLYGVETGALPASVMDDYINRVWQK | 224 - 251 |
| 2013.01 | YTTTTLTVTPFGDRPDTK | 252 - 269 |
| 3343.57 | VSGNVMNFTNTSGAVVTSFQKPDASSVFGCHR | 274 - 305 |
| 1139.59 | LLDAPNDQVR | 306 - 315 |
| 880.42 | TLCAGFNR | 321 - 328 |
| 2953.41 | TLCAGFNRSTLLSNPNQPDPSAANFYR | 321 - 347 |
| 2091.00 | STLLSNPNQPDPSAANFYR | 329 - 347 |
| 3144.50 | STLLSNPNQPDPSAANFYRDPVTNHYAR | 329 - 356 |
| 1071.51 | DPVTNHYAR | 348 - 356 |
| 666.38 | IIHER | 357 - 361 |
| 3203.44 | MADGKAYAFAFDDVGNHESLVHDGNPAEAR | 362 - 391 |
| 2701.22 | AYAFAFDDVGNHESLVHDGNPAEAR | 367 - 391 |
| 741.43 | LTLAPLD | 392 - 398 |

The left column "Mass" shows the molecular mass of the peptide in Dalton.
The middle column "Peptide" shows the amino acid sequence of the matching peptide as deduced from the NCBI genbank.
The right column shows the amino acid positions in the sequence of the beta-1,3-glucanase of *Streptomyces coelicolor* A3 where the peptide of the second column is found.

TABLE 3

| Peptide Nr | SEQ ID No. | # Amino acids | Amino acid sequence | Amino acid positions in the sequence of the beta-1,3-glucanase of *Streptomyces coelicolor* A3 |
|---|---|---|---|---|
| 1 | 1 | 8 | IYFSYGQK | 114-121 |
| 2 | 2 | 67 | LTTGGLVQPAVQNPSDPNRNILFNWSEYTLNDGGLWLNSTQVDMFSAPYTVGVQRADGGVTSAGQLK | 126-192 |
| 3 | 3 | 72 | GVFDALRAQPGWGGLIQTRPDGTVLRALAPLYGVETGALPASVMDDYINRVWQKYTTTTLTVTPFGDRPDTK | 198-269 |
| 4 | 4 | 42 | VSGNVMNFTNTSGAVVTSFQKPDASSVFGCHRLLDAPNDQVR | 274-315 |

TABLE 3-continued

| Peptide Nr | SEQ ID No. | # Amino acids | Amino acid sequence | Amino acid positions in the sequence of the beta-1,3-glucanase of *Streptomyces coelicolor* A3 |
|---|---|---|---|---|
| 5 | 5 | 78 | TLCAGFNRSTLLSNPNQPDPSAANFYRD PVTNHYARIIHERMADGKAYAFAFDDVG NHESLVHDGNPAEARLTLAPLD | 321-398 |

TABLE 4

Amino acid sequence of the laminaripentaose-producing-β-1, 3-glucanase of *Streptomyces coelicolor* A3.

The highlighted sequences represent the 5 unique peptide sequences from Table 3 above.

MLSRLRHRLL AVAAAAGLTG ALLSFGAAPP ADAAVPATIP LKITNNSARG 50

DAVHIYNLGT SLTTGQQGWA DENGTFHAWP AGGNPPTPAP DASIPGPAAG 100

QTKTIRIPKL SGRIYFSYGQ KLDFRLTTGG LVQPAVQNPS DPNRNILFNW 150

SEYTLNDGGL WLNSTQVDMF SAPYTVGVQR ADGGVTSAGQ LKAGGYRGVF 200

DALRAQPGWG GLIQTRPDGT VLRALAPLYG VETGALPASV MDDYINRVWQ 250

KYTTTTLTVT PFGDRPDTKY FGRVSGNVMN FTNTSGAVVT SFQKPDASSV 300

FGCHRLLDAP NDQVRGPISR TLCAGFNRST LLSNPNQPDP SAANFYRDPV 350

TNHYARIIHE RMADGKAYAF AFDDVGNHES LVHDGNPAEA RLTLAPLD 398

The underlined part is the putative signal sequence based on studies with the homologous β-1,3-glucanase of *Streptomyces matensis* DIC-108 (Nakanayashi et al. (1998), J. Fermentation and Bioengineering 85 (5), 459-464). The amino acid sequence of the mature enzyme therefore would start with Ala at position 34. The highlighted amino acids represent the 5 peptides as depicted in Table 3.

TABLE 5

Amino acid sequence alignment of the laminaripentaose-producing-8-1,3-glucanase of *Streptomyces coelicolor* A3 with the β-1,3-glucanase *Streptomyces matensis* DIC-108

| | | |
|---|---|---|
| S. coelicolor | 1 MLSRLRHRLLAVA--AAAGLTGALLSFGAAPPADAAVPATIPLKITNNSA | 48 |
| | \|\|..\|\|.\|:.\|\|\| .\|..\|.\|..\|:.\|...\| \|.\|\|\|\|\|\|\|\|\|.\|\|\|\|. | |
| S. matensis | 1 MLRTLRRRVTAVALGLATALGGGWLAAGVPSPAHAAVPATIPLTITNNSG | 50 |
| S. coelicolor | 49 RGDAVHIYNLGTSLTTGQQGWADENGTFHAWPAGGNPPTPAPDASIPGPA | 98 |
| | \|.:.:\|\|\|\|\|\|\|.\|::\|:\|\|\|\|.:\|.\|\|.\|\|\|\|\|\|\|\|\|\|\|\|\|\|\|\|\| | |
| S. matensis | 51 RAEQIHTYNLGTELSSGRQGWADASGAFHPWPAGGNPPTPAPDASIPGPA | 100 |
| S. coelicolor | 99 AGQTKTIRIPKLSGRIYFSYGQKLDFRLTTGGLVQPAVQNPSDPNRNILF | 148 |
| | .\|::.\|\|:\|\|\|.\|\|\|\|\|\|\|\|\|:\|::\|\|\|\|\|\|\|\|\|\|\|\|\|\|\|:\|\|\|\|:\|\|\| | |
| S. matensis | 101 PGRSTTIQIPKFSGRIYFSYGRKMEFRLTTGGLVQPAVQNPTDPNRDILF | 150 |
| S. coelicolor | 149 NWSEYTLNDGGLWLNSTQVDMFSAPYTVGVQRADGGVTSAGQLKAGGYRG | 198 |
| | \|\|\|\|\|\|\|\|\|.\|\|\|:\|\|\|\|\|\|\|\|\|\|\|\|:\|.\|\|...\|.\|:\|:.\|\|\|.\| | |
| S. matensis | 151 NWSEYTLNDSGLWINSTQVDMESAPYTVGVRRGDTTLSTGKLRPGGYNG | 200 |
| S. coelicolor | 199 VFDALRAQP-GWGGLIQTRPDGTVLRALAPLYGVETGALPASVMDDYINR | 247 |
| | \|\|:\|\|\|.\|. \|\|..\|\|\|\|\|.\|\|\|\|\|\|\|\|:\|\|\|\|\|\|\|\|\|\|\|\|\|\|\|\|\| | |
| S. matensis | 201 VFNALRGQSGGWANLIQTRSDGTVLRALSPLYGVETGALPASVMDDYINR | 250 |
| S. coelicolor | 248 VWQKYTTTTLTVTPFGDRPDTKYFGRVSGNVMNFTNTSGAVVTSFQKPDA | 297 |
| | \|\|.\|\|\|\|.\|.\|.\|\|\|\|.\|\|\|\|.:\|.\|\|\|\|\|.\|:.\|\|:.\|\|\|\|\|\|:\|\|\|\|\| | |
| S. matensis | 251 VWNKYTGTDLIVITFADRPDVRYTGRVSGGVLRFTDGSGAVVTTFQKPDA | 300 |

TABLE 5-continued

Amino acid sequence alignment of the laminaripentaose-producing-8-1,3-glucanase of Streptomyces coelicolor A3 with the β -1,3-glucanase Streptomyces matensis DIC-108

```
S. coelicolor  298 SSVFGCHRLLDAPNDQVRGPISRTLCAGFNRSTLLSNPNQPDPSAANFYR  347
                   |||||||||||||||||||||||||||||:|||:||:|||.|||.||:
S. matensis    301 SSVFGCHRLLDAPNDQVRGPISRTLCAGFNRTTLLANPHQPDRSAAGFYQ  350

S. coelicolor  348 DPVTNHYARIIHERMADGKAYAFAFDDVGNHESLVHDGNPAEARLTLAPL  397
                   :||||||||||..||||||.||||||:|||||||||:|..|.|||.|.
S. matensis    351 EPVTNHYARIIHAHMADGKAYGFAFDDVGHHESLVHDGDPRGASLTLDPF  400

S. coelicolor  398 D                                                   398
                   |
S. matensis    401 D                                                   401
```

The alignment of the laminaripentaose-producing-β-1,3-glucanase of Streptomyces coelicolor A3 with the laminaripentaose-producing-β-1,3-glucanase Streptomyces matensis DIC-10 reveals that the sequence are 76.3% identical based on the length of 401 residues. In the amino acid sequence of laminaripentaose-producing-β-1,3-glucanase of Streptomyces coelicolor A3 3 gaps were introduced.

Example 2

Solubilisation of Yeast Cell Wall Glucans with Acid and Alkali

Isolated yeast cell walls are commercially available from various suppliers. For the present example, isolated yeast cell walls were obtained as a side product of yeast extract production. The yeast cells walls contained 31.7% glucans based on dry matter.

The yeast cell walls were incubated for 16 hours at 95° C. and at a pH value indicated in the table below. After the incubation, the sample was heated for 15 minutes at 100° C. and after lyophilisation, the yeast cell walls were dissolved in $D_2O$ or DMSO as described in the Materials and Methods.

conditions solubilised the glucans for a minor part: 2.8-5.3% of the total glucans in the yeast cell walls could be solubilised.

In untreated yeast cell walls 13.2% of the total β-glucans were solubilised in DMSO. Solubilisation under acidic conditions increased the amount DMSO soluble β-glucans substantially (21 and 30%). At pH 5.5 and 10.0 the fraction of DMSO soluble β-glucans did not change or even slightly decreased. Solubilisation under alkaline conditions at pH 12 did not result in solubilized β-glucans.

Example 3

Solubilisation of Yeast Cell Wall Glucans Using Laminaripentaose-Producing-β-1,3-Glucanase Isolated yeast cell walls were incubated for 16 hours at 55° C. and at pH=5.5 with or without the indicated amounts of Denazyme GEL-L1 (wt % dm means "weight percent" of the enzyme solution based on yeast cell wall dry matter—for instance, 0.01 wt % dm is equal to 0.1 mg Denazyme solution per gram dry weight yeast cell walls). After the incubation, the sample was heated for 15 minutes at 100° C. and after lyophilisation, the yeast cell walls were dissolved in $D_2O$ or DMSO as described in the Materials and Methods.

TABLE 6

| Incubation | pH | Water soluble β-glucans | | DMSO soluble β-glucans | | Ratio | Ratio |
| --- | --- | --- | --- | --- | --- | --- | --- |
| | | % dm | Rel % | % dm | Rel % | DMSO/water | water/DMSO |
| Control | No incubation | N.D.* | N.D.* | 4.2 | 13.2% | ∞ | 0 |
| 1 | 2.0 | 1.7 | 5.3% | 9.5 | 30.0% | 5.7 | 0.18 |
| 2 | 3.0 | 0.9 | 2.8% | 6.7 | 21.1% | 7.5 | 0.13 |
| 3 | 5.5 | N.D.* | N.D.* | 4.3 | 13.5% | ∞ | 0 |
| 4 | 10.0 | N.D.* | N.D.* | 2.7 | 8.5% | ∞ | 0 |
| 5 | 12.0 | N.D.* | N.D.* | N.D.* | N.D.* | n.a. | n.a. |

*N.D. = not detectable (i.e. below the detection limit)

The results in Table 6 show that the yeast cell wall β-glucans cannot be water-solubilized at a pH of 5.5 or at an alkaline pH of 10 or 12. Solubilisation under more acidic After incubating for 30 minutes at 50° C., the samples were centrifuged for 10 minutes and the supernatant analysed by NMR as described in the Materials and Methods.

TABLE 7

|  | [Denazyme] | Water soluble β-glucans | | DMSO soluble β-glucans | | Ratio | Ratio |
|---|---|---|---|---|---|---|---|
| Incubation | in mixture | % dm | Rel % | % dm | Rel % | DMSO/water | water/DMSO |
| Control | No incubation | N.D.* | N.D.* | 4.2 | 13.2% | ∞ | 0 |
| 6 | 0.0 | N.D.* | N.D.* | 3.8 | 11.9% | ∞ | 0 |
| 7 | 0.01 wt % dm | N.D.* | N.D.* | 12.6 | 39.7% | ∞ | 0 |
| 8 | 0.04 wt % dm | 6 | 18.9% | 14.7 | 46.4% | 2.5 | 0.4 |

*N.D. = not detectable (i.e. below the detection limit)

The results in Table 7 show that incubation of yeast cell walls with laminaripentaose-producing-β-1,3-glucanase (Denazyme GEL-L1) increases the solubility of the β-glucans fraction in DMSO significantly whereas the solubility in water increases only with the highest enzyme concentration.

Comparative Example 4

Solubilisation of Yeast Cell Wall Glucans Using Laminarinase

Isolated yeast cell walls were incubated for 16 hours at 55° C. and at pH=5.3 with or without the indicated amounts of laminarinase (wt % dm means "weight percent" of the enzyme solution based on yeast cell wall dry matter—for instance, 0.01 wt % dm is equal to 0.1 mg laminarinase solution per gram dry weight yeast cell walls). After the incubation, the sample was heated for 15 minutes at 100° C. and after lyophilisation, the yeast cell walls were dissolved in $D_2O$ or DMSO as described in the Materials and Methods.

After incubating for 30 minutes at 50° C., the samples were centrifuged for 10 minutes and the supernatant analysed by NMR as described in the Materials and Methods. The yeast cell walls contained 37% glucan.

TABLE 8

|  | [Laminarinase] | Water soluble β-glucans | | DMSO soluble β-glucans | |
|---|---|---|---|---|---|
| Incubation | In mixture | % dm | Rel % | % dm | Rel % |
| 9 | 0.0 | N.D.* | N.D.* | 3.0 | 8.1 |
| 10 | 0.01 wt % dm | N.D.* | N.D.* | 2.9 | 7.8 |
| 11 | 0.04 wt % dm | N.D.* | N.D.* | 3.1 | 8.4 |

*N.D. = not detectable (i.e. below the detection limit)

The results in Table 8 clearly indicate that laminarinase is not able to solubilize the glucans present in the yeast cell walls.

Example 5

In Vitro Study on IL-6 and IL-10 Secretion

Isolated peripheral blood mononuclear cells (PMBC's) (macrophages, monocytes, B and T cells) from 2 pigs were incubated in a medium including β-glucans from untreated yeast cell walls or acid treated yeast cell walls obtained from example 2. IL-6 is a pro-inflammatory cytokine that is released at the beginning of the immune response while IL-10 is an anti-inflammatory cytokine.

FIGS. 4 and 5 show that there is a stimulatory effect on the IL 6 and IL 10 secretion after addition of the β-glucans from acid treated yeast cell walls at pH 3 of Example 2, incubation 2 in comparison to the β-glucans from non-treated yeast cell walls of Example 2 (control).

Example 6

In Vitro Study on Production of Reactive Oxygen Species

The immunomodulating effect of β-glucans from acid treated yeast cell walls of Example 2, enzyme treated yeast cell walls of Example 3, incubation no. 7 and commercial wheat yeast concentrate (market reference) was tested on neutrophils and on monocytes isolated from two pigs able to produce reactive oxygen species (ROS). The reactive oxygen species (ROS) production after addition of the samples to the cell medium at different concentrations, is a measure of the non-specific defence against pathogens. Hanks Balanced Salt Solution (HBSS) was used as a negative control.

The data in FIGS. 6 and 7 clearly indicate that there was a dose response identified for all β-glucan containing samples applied. The acid treated yeast cell walls of Example 2, enzyme treated yeast cell walls of Example 3, incubation no. 7 and commercial wheat yeast concentrate (market reference) triggered ROS production by neutrophils at a β-glucan concentration of 50 and 200 µg/ml.

The acid treated yeast cell walls of Example 2 and the enzyme treated yeast cell walls of Example 3, incubation no. 7 showed an improved stimulatory effect on the production of O-radicals compared to the commercial wheat yeast concentrate (market reference).

FIGS. 8 and 9 clearly show that the β-glucan present in commercial wheat yeast concentrate did not trigger the ROS production by monocytes at the tested concentrations. The β-glucan present in the acid treated yeast cell walls of Example 2 and the enzyme treated yeast cell walls of Example 3, incubation no. 7 showed an triggered 0-radicals production. However the dose-response effect differed for both pigs.

Example 7

In Vivo Study on Broiler Chickens

During the in-vivo study with several groups of 3000 broiler chickens the following parameters were determined after feeding the broiler chickens with standard starter feed without added β-glucans (control) or with a standard starter feed comprising 50 mg of β-glucans per kg feed (test). This 50 mg of β-glucans originated from a combination of β-glucans from standard wheat yeast concentrate (25 mg) and β-glucans from acid treated yeast cell walls (25 mg). The starter feed comprising 50 mg of β-glucans was only fed during the start of the feed trial, i.e. for the initial 10 days. The feed trial was continued for 35 days with standard starter feed for both groups (control and test). At the end of the feed trial the following parameters were determined: total feed consumed (kg), total meat at end of feed trial (kg), the average weight per chicken (g), the feed conversion ratio 1500 g, blood samples were taken and the serum was analysed on the natural immune system response via ELISA (IgM and IgG concentrations).

TABLE 9

| Sample | Solubilisation | Total feed (kg) | Total meat (kg) | Avg. chicken weight (g) | Feed Conversion Ratio 1500 g (FCR 1500 g) (—) | Immune data IgM/IgG (—) |
|---|---|---|---|---|---|---|
| Standard starter feed comprising 50 mg of β-glucans partially originated from acid treated yeast cell walls from Example 2 no. 2 | With pH 3.0 | 12280 | 7500 | 2577 | 1.206 | 6.51/5.08 |
| Standard starter feed (Control) | no | 11640 | 7130 | 2531 | 1.220 | 5.94/4.82 |

The results in Table 9 clearly showed that the broiler chickens fed with standard starter feed comprising β-glucans partially originating from acid treated yeast cell walls, showed after the 35 days feed trial an improved average chicken weight, an improved feed conversion ratio 1500 g (FCR 1500 g) and an increased immune response for both IgM and IgG.

Example 8

In Vivo Study on Broiler Chickens

In-vivo study with several groups of approximately 34000 broiler chickens that were fed with a standard starter feed comprising added β-glucans during the initial 10 days of the trial. A control group of 35000 broiler chickens was fed with the standard starter feed only. The standard starter feed comprising added β-glucans contained 50 mg of β-glucans per kg feed originated from a combination of β-glucans from standard wheat yeast concentrate (25 mg) and β-glucans from acid treated yeast cell walls (25 mg). At the end of the chicken feed trial (after 35 days) the following parameters were determined: total feed consumed (kg), total meat at end of feed trial (kg), the average weight per chicken (g), the feed conversion ratio 1500 g and the lethality of the broiler chickens was recorded.

TABLE 10

| Sample | Solubilisation | Total feed (kg) | Total meat (kg) | Avg. chicken weight (g) | Feed conversion Ratio 1500 g (FCR 1500 g) (—) | Lethality (%) |
|---|---|---|---|---|---|---|
| Standard starter feed comprising 50 mg of β-glucans partially originated from acid treated yeast cell walls from Example 2 no. 2 | With pH 3.0 | 116388 | 71876 | 2450 | 1.240 | 8.6 |
| Standard starter feed (Control) | no | 119729 | 74220 | 2374 | 1.264 | 10.7 |

The results in Table 10 clearly showed that the broiler chickens fed with standard starter feed comprising 50 mg of β-glucans partially originating from acid treated yeast cell walls had an increased average weight, the feed conversion ratio 1500 g improved and finally the lethality was clearly reduced.

The invention claimed is:

1. A process for the treatment of a composition comprising yeast cell walls comprising β-1,3-glucans which are insoluble when extracted with water and partially soluble when extracted with dimethyl sulfoxide (DMSO), the process comprising contacting said composition with laminaripentaose-producing-β-1,3-glucanase followed by inactivating the laminaripentaose-producing-β-1,3-glucanase to result in a second composition comprising yeast cell walls wherein the second composition comprises a higher percentage of the β-1,3-glucans relative to the total β-1,3-glucans which are soluble in DMSO compared to the percentage of β-1,3-glucans in untreated yeast cell walls, and wherein the ratio of the β-1,3-glucans soluble in DMSO compared to water is greater than or equal to 2, wherein the laminaripentaose-producing-β-1,3-glucanase comprises an amino acid sequence selected from the group consisting of SEQ ID NO: 1, SEQ ID NO: 2, SEQ D NO: 3, SEQ ID NO: 4, SEQ ID NO: 5, SEQ ID NO: 6 and SEQ ID NO: 7 or an amino acid sequence 70% or more identical to SEQ ID NO: 6 or SEQ ID NO: 7.

2. The process according to claim 1, wherein the inactivating comprises heating said composition to a temperature above 70° C. for a time sufficient to inactivate the laminaripentaose-producing-β-1,3-glucanase.

3. The process according to claim 1, wherein the laminaripentaose-producing-β-1,3-glucanase is from *Streptomyces coelicolor* A3 having the amino acid sequence depicted in SEQ ID NO: 6 or an amino acid sequence which is 70% or more identical to SEQ ID: NO: 6.

4. The process according to claim 1, wherein the laminaripentaose-producing-β-1,3-glucanase is from *Streptomyces matensis* DIC-108 having the amino acid sequence depicted in SEQ ID NO: 7 or an amino acid sequence which is 70% or more identical to SEQ ID: NO: 7.

5. The process according to claim 1 wherein the process of the invention is carried out at a pH between 2 and 9.

6. The process according to claim 1 wherein the process of the invention is carried out at a temperature between 20° C. and 90° C.

7. The process of claim 1, wherein more than 15% of the β-1,3-glucans in the second composition are soluble in DMSO.

8. The process of claim 1, wherein the second composition comprises laminaripentaose produced by the laminaripentaose-producing-β-1,3-glucanase in an amount of less than about 30% of the total glucose units present in the second composition.

9. The process of claim 1, wherein the second composition comprising yeast cell walls wherein a higher percentage of the β-1,3-glucans are soluble in DMSO compared to the percentage of β-1,3-glucans in a composition of yeast cells walls treated with laminarinase.

10. The process of claim 2, wherein the pH is 5.5.

11. The process of claim 1, wherein the DMSO solubility is determined by incubation of 100 mg of the β-1,3-glucans in DMSO at 50° C. for 30 minutes.

12. The process of claim 1, wherein the water solubility is determined by dissolving 15 mg of β-1,3-glucans in 0.5 ml of distilled water at pH 8.5.

* * * * *